(12) United States Patent
Endo

(10) Patent No.: US 10,524,635 B2
(45) Date of Patent: Jan. 7, 2020

(54) ENDOSCOPE, RECEPTION DEVICE, WIRELESS ENDOSCOPE SYSTEM, IMAGE TRANSMISSION METHOD, IMAGE RECEPTION METHOD, AND NON-TRANSITORY COMPUTER READABLE RECORDING MEDIUM STORING PROGRAM

(71) Applicant: OLYMPUS CORPORATION, Hachioji-shi, Tokyo (JP)

(72) Inventor: Takahisa Endo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 511 days.

(21) Appl. No.: 15/333,828

(22) Filed: Oct. 25, 2016

(65) Prior Publication Data
US 2017/0035272 A1 Feb. 9, 2017

Related U.S. Application Data

(63) Continuation of application No. PCT/JP2015/061954, filed on Apr. 20, 2015.

(30) Foreign Application Priority Data

May 28, 2014 (JP) ................................. 2014-110594

(51) Int. Cl.
*A61B 1/00* (2006.01)
*A61B 1/04* (2006.01)
(Continued)

(52) U.S. Cl.
CPC ...... *A61B 1/00016* (2013.01); *A61B 1/00009* (2013.01); *A61B 1/04* (2013.01);
(Continued)

(58) Field of Classification Search
CPC ... A61B 1/00016; A61B 1/00009; A61B 1/04; G02B 23/24; G02B 23/2484;
(Continued)

(56) References Cited

U.S. PATENT DOCUMENTS

2006/0209176 A1 9/2006 Nakamura et al.
2006/0217591 A1* 9/2006 Abe ................... A61B 1/00016
600/118

(Continued)

FOREIGN PATENT DOCUMENTS

JP 3247349 B 1/2002
JP 2006-279927 A 10/2006
(Continued)

OTHER PUBLICATIONS

International Search Report dated Sep. 8, 2016 issued in counterpart International Application No. PCT/JP2015/061954 (2 pages).

(Continued)

*Primary Examiner* — John P Leubecker
*Assistant Examiner* — Shankar Raj Ghimire
(74) *Attorney, Agent, or Firm* — Westerman, Hattori, Daniels & Adrian, LLP

(57) ABSTRACT

An endoscope includes an imaging unit configured to image a subject and output image data, a moving-image generation unit configured to generate moving-image data from the image data output from the imaging unit, a still-image generation unit configured to generate still-image data from the image data output from the imaging unit, a release instruction unit configured to receive an image-recording instruction from a user, a first wireless communication unit configured to sequentially change a wireless channel to transmit test data and transmit the still-image data to the reception device when the release instruction unit receives the image-recording instruction, a second wireless commu- (Continued)

nication unit configured to transmit the moving-image data to the reception device using a wireless channel different from the wireless channel currently used by the first wireless communication unit, and a first setting unit configured to set a wireless channel determined from communication quality information.

8 Claims, 29 Drawing Sheets

(51) Int. Cl.
*G02B 23/24* (2006.01)
*H04N 5/225* (2006.01)
*G06F 11/14* (2006.01)
*G06F 11/22* (2006.01)

(52) U.S. Cl.
CPC ......... *G02B 23/24* (2013.01); *G02B 23/2484* (2013.01); *G06F 11/14* (2013.01); *H04N 5/2256* (2013.01); *G06F 11/1443* (2013.01); *G06F 11/221* (2013.01); *H04N 2005/2255* (2013.01)

(58) Field of Classification Search
CPC ........ G06F 11/1443; H04N 2005/2255; H04N 7/183; H04W 72/10; H04W 36/06
See application file for complete search history.

(56) References Cited

U.S. PATENT DOCUMENTS

| | | | | |
|---|---|---|---|---|
| 2008/0253462 | A1* | 10/2008 | Singh | H04L 1/0003 375/240.25 |
| 2009/0257487 | A1* | 10/2009 | Wang | H04B 7/0617 375/240.02 |
| 2010/0128688 | A1* | 5/2010 | Song | H04W 72/10 370/329 |
| 2010/0296434 | A1* | 11/2010 | Amagai | H04W 48/12 370/315 |
| 2011/0257481 | A1* | 10/2011 | Ogawa | A61B 1/00016 600/109 |
| 2012/0062715 | A1* | 3/2012 | Endo | A61B 1/00016 348/65 |
| 2012/0134410 | A1 | 5/2012 | Kawasaki et al. | |
| 2012/0200685 | A1* | 8/2012 | Kawasaki | A61B 1/00006 348/65 |
| 2013/0034825 | A1* | 2/2013 | Phillips | A61B 1/00016 433/29 |
| 2015/0208900 | A1* | 7/2015 | Vidas | A61B 1/00009 348/74 |

FOREIGN PATENT DOCUMENTS

| | | |
|---|---|---|
| JP | 2008-142153 A | 6/2008 |
| JP | 2009-247407 A | 10/2009 |
| JP | 2010-284274 A | 12/2010 |
| JP | 2010-288186 A | 12/2010 |
| JP | 2012-110478 A | 6/2012 |

OTHER PUBLICATIONS

Office Action dated Apr. 17, 2018, issued in counterpart Japanese application No. 2014-110594, with English translation. (5 pages).

* cited by examiner

ENDOSCOPE, RECEPTION DEVICE, WIRELESS ENDOSCOPE SYSTEM, IMAGE TRANSMISSION METHOD, IMAGE RECEPTION METHOD, AND NON-TRANSITORY COMPUTER READABLE RECORDING MEDIUM STORING PROGRAM

This application is a continuation application based on a PCT International Application No. PCT/JP2015/061954, filed on Apr. 20, 2015, whose priority is claimed on Japanese Patent Application No. 2014-110594, filed May 28, 2014. The contents of both the PCT International Application and the Japanese Patent Application are incorporated herein by reference.

BACKGROUND OF THE INVENTION

Field of the Invention

The present invention relates to technology used in a wireless endoscope system.

Description of Related Art

In recent years, endoscope devices that can capture an image of a subject within a body cavity or a duct by an elongated insertion unit inserted into the body cavity or the duct and cause the acquired image of the subject to be capable of being observed on a monitor have been widely used. In such endoscope devices, an endoscope having the insertion unit is connected to an external device through a light-guide cable which guides illumination light generated by a light source device to the endoscope, or a signal cable through which a video obtained by the endoscope is transmitted to a video processor. Therefore, a movement range of the endoscope is limited and the operability of the endoscope is interfered.

Thus, a wireless endoscope system which wirelessly transmits a video obtained by the endoscope has been considered. In the wireless endoscope system, the limitation of the movement range of the endoscope is mitigated and the operability is improved.

In the wireless endoscope system, image data is often transmitted in a compressed state because the transmission band is limited. A function of saving a video of a specific portion designated by a user operating an operation switch as a still image, i.e., a release function, is used to confirm the video of the specific portion after the endoscopic procedure. This still image is saved as data used for reviewing the specific portion in detail. Thus, it is necessary for the still image to have higher resolution than a video at the time of normal observation.

Therefore, the transmission of still-image data used for saving a high-resolution still image at the time of using the release function is necessary in addition to transmission of compressed moving-image data in the normal observation. This still-image data is still-image data having a lower compression rate than moving-image data or uncompressed still-image data.

In Japanese Patent No. 3247349, a moving-image-monitoring device which simultaneously transmits moving-image video data and selected still-image video data through the same transmission path is disclosed.

SUMMARY OF THE INVENTION

According to a first aspect of the present invention, an endoscope includes: an imaging unit configured to image a subject and output image data; a moving-image generation unit configured to generate moving-image data from the image data output from the imaging unit; a still-image generation unit configured to generate still-image data from the image data output from the imaging unit; a release instruction unit configured to receive an image-recording instruction from a user; a first wireless communication unit configured to sequentially change a wireless channel to transmit test data used for detecting communication quality of each of a plurality of wireless channels to a reception device and transmit the still-image data to the reception device when the release instruction unit receives the image-recording instruction; a second wireless communication unit configured to transmit the moving-image data to the reception device using a wireless channel different from the wireless channel currently used by the first wireless communication unit; and a first setting unit configured to set a wireless channel in the second wireless communication unit, wherein the wireless channel is determined from communication quality information regarding the communication quality of the wireless channel used in the transmission of the test data.

According to a second aspect of the present invention, in the endoscope according to the first aspect, the first wireless communication unit may sequentially change the wireless channel at a previously designated time interval to transmit the still-image data to the reception device, when the release instruction unit receives the image-recording instruction.

According to a third aspect of the present invention, in the endoscope according to the first aspect, the first wireless communication unit may transmit the still-image data to the reception device using only one wireless channel, when the release instruction unit receives the image-recording instruction.

According to a fourth aspect of the present invention, in the endoscope according to the first aspect, the first wireless communication unit or the second wireless communication unit may receive wireless channel information indicating a wireless channel determined from the communication quality information from the reception device, and the first setting unit may set the wireless channel indicated by the wireless channel information in the second wireless communication unit.

According to a fifth aspect of the present invention, in the endoscope according to the first aspect, the first wireless communication unit or the second wireless communication unit may receive reception information indicating that the test data is received from the reception device, and the first setting unit may generate the communication quality information on the basis of the reception information, determine a wireless channel on the basis of the generated communication quality information, and set the determined wireless channel in the second wireless communication unit.

According to a sixth aspect of the present invention, in the endoscope according to the first aspect, the first setting unit may set the wireless channel determined from the communication quality information in the second wireless communication unit, when the communication quality of the wireless channel used by the second wireless communication unit is less than predetermined quality.

According to a seventh aspect of the present invention, in the endoscope according to the first aspect, the first wireless communication unit may transmit information used for identifying the test data and the still-image data to the reception device.

According to an eighth aspect of the present invention, a reception device includes: a third wireless communication unit configured to sequentially change a wireless channel to receive test data used for detecting communication quality of each of a plurality of wireless channels from an endoscope, and receive still-image data from the endoscope; a fourth wireless communication unit configured to receive moving-image data from the endoscope using a wireless channel different from the wireless channel used by the third wireless communication unit; and a second setting unit configured to set a wireless channel determined from communication quality information regarding the communication quality of the wireless channel used in the transmission of the test data in the fourth wireless communication unit.

According to a ninth aspect of the present invention, a wireless endoscope system includes an endoscope and a reception device, wherein the endoscope includes: an imaging unit configured to image a subject and output image data; a moving-image generation unit configured to generate moving-image data from the image data output from the imaging unit; a still-image generation unit configured to generate still-image data from the image data output from the imaging unit; a release instruction unit configured to receive an image-recording instruction from a user; a first wireless communication unit configured to sequentially change a wireless channel to transmit test data used for detecting communication quality of each of a plurality of wireless channels to a reception device and transmit the still-image data to the reception device when the release instruction unit receives the image-recording instruction; a second wireless communication unit configured to transmit the moving-image data to the reception device using a wireless channel different from the wireless channel currently used by the first wireless communication unit; and a first setting unit configured to set a wireless channel in the second wireless communication unit, the wireless channel being determined from communication quality information regarding the communication quality of the wireless channel used in the transmission of the test data, and wherein the reception device includes: a third wireless communication unit configured to sequentially change a wireless channel to receive test data and receive still-image data; a fourth wireless communication unit configured to receive moving-image data using a wireless channel different from the wireless channel used by the third wireless communication unit; and a second setting unit configured to set a wireless channel determined from communication quality information in the fourth wireless communication unit.

According to a tenth aspect of the present invention, an image transmission method includes the steps of: transmitting, by a first wireless communication unit, test data used for detecting communication quality of each of a plurality of wireless channels to a reception device while sequentially changing a wireless channel; transmitting, by the first wireless communication unit, still-image data generated from image data output from an imaging unit to the reception device when an image-recording instruction is received from a user; transmitting, by a second wireless communication unit, moving-image data generated from the image data to the reception device using a wireless channel different from the wireless channel currently used by the first wireless communication unit; and setting, by a first setting unit, a wireless channel determined from communication quality information about the communication quality of the wireless channel used in the transmission of the test data in the second wireless communication unit.

According to an eleventh aspect of the present invention, an image reception method includes the steps of: receiving, by a third wireless communication unit, test data used for detecting communication quality of each of a plurality of wireless channels from an endoscope while sequentially changing a wireless channel; receiving, by the third wireless communication unit, still-image data from the endoscope; receiving, by a fourth wireless communication unit, moving-image data from the endoscope using a wireless channel different from the wireless channel used by the third wireless communication unit; and setting, by a second setting unit, a wireless channel determined from communication quality information regarding the communication quality of the wireless channel used in the transmission of the test data in the fourth wireless communication unit.

According to a twelfth aspect of the present invention, a non-transitory computer readable recording medium storing a program causes a computer to execute the steps of: transmitting, by a first wireless communication unit, test data used for detecting communication quality of each of a plurality of wireless channels to a reception device while sequentially changing a wireless channel; transmitting, by the first wireless communication unit, still-image data generated from image data output from an imaging unit to the reception device when an image-recording instruction is received from a user; transmitting, by a second wireless communication unit, moving-image data generated from the image data to the reception device using a wireless channel different from the wireless channel currently used by the first wireless communication unit; and setting, by a first setting unit, a wireless channel determined from communication quality information regarding the communication quality of the wireless channel used in the transmission of the test data in the second wireless communication unit.

According to a thirteenth aspect of the present invention, a non-transitory computer readable recording medium storing a program causes a computer to execute the steps of: receiving, by a third wireless communication unit, test data used for detecting communication quality of each of a plurality of wireless channels from an endoscope while sequentially changing a wireless channel; receiving, by the third wireless communication unit, still-image data from the endoscope; receiving, by a fourth wireless communication unit, moving-image data from the endoscope using a wireless channel different from the wireless channel used by the third wireless communication unit; and setting, by a second setting unit, a wireless channel determined from communication quality information about the communication quality of the wireless channel used in the transmission of the test data in the fourth wireless communication unit.

DETAILED DESCRIPTION OF THE INVENTION

Figure 1:
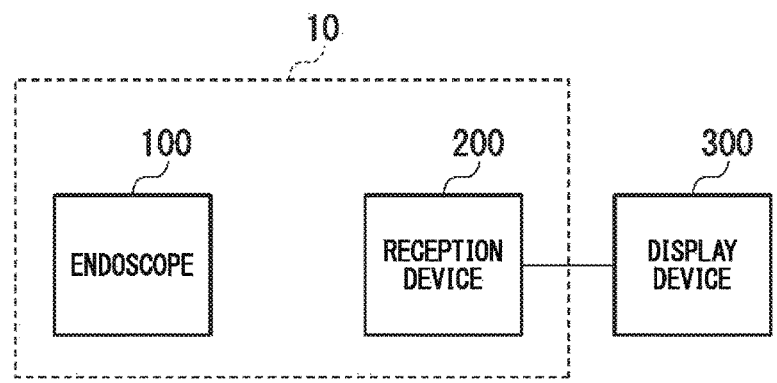
FIG. 1 is a block diagram illustrating a configuration example of a wireless endoscope system according to an embodiment of the present invention.

Hereinafter, embodiments of the present invention will be described with reference to the drawings. FIG. 1 illustrates a configuration example of a wireless endoscope system 10 according to the present embodiment. As illustrated in FIG. 1, the wireless endoscope system 10 includes an endoscope 100 and a reception device 200. The endoscope 100 and the reception device 200 perform wireless communication. The reception device 200 is connected to a display device 300 through a cable or the like.

Figure 2:
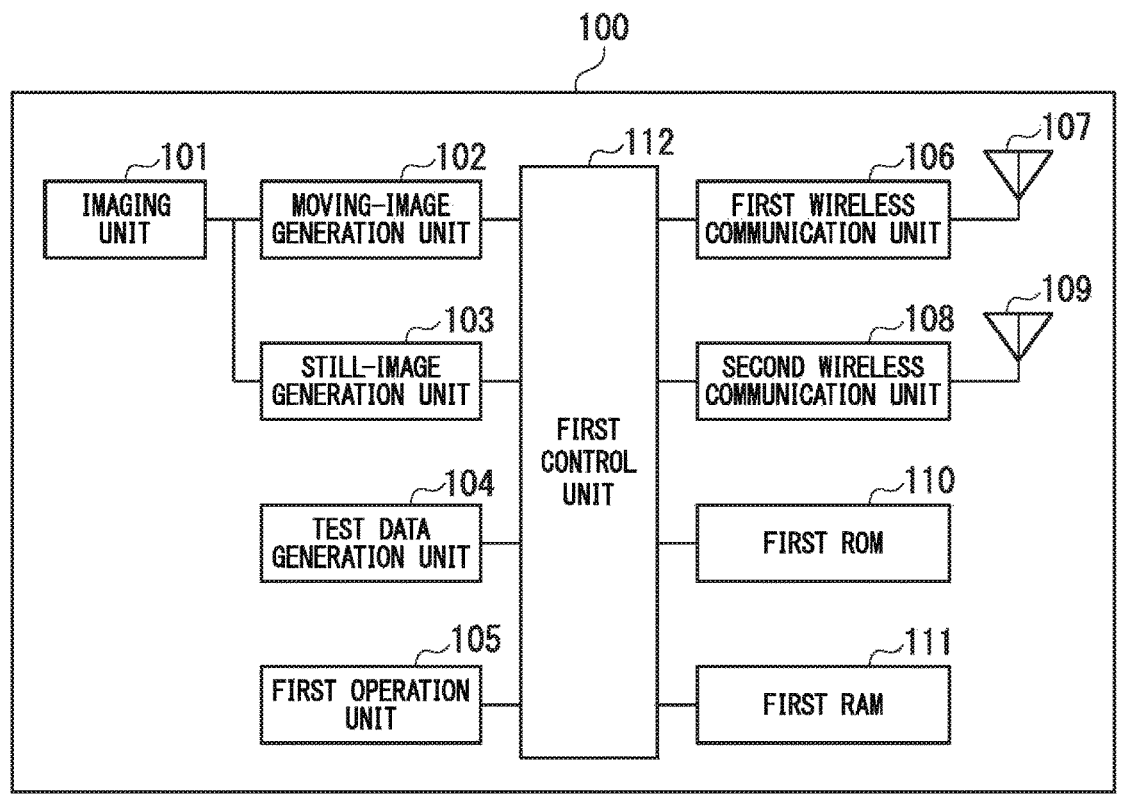
FIG. 2 is a block diagram illustrating a configuration example of an endoscope according to an embodiment of the present invention.

FIG. 2 illustrates an electrical configuration example of the endoscope 100. As illustrated in FIG. 2, the endoscope 100 includes an imaging unit 101, a moving-image generation unit 102, a still-image generation unit 103, a test data generation unit 104, a first operation unit 105, a first wireless communication unit 106, a first antenna 107, a second wireless communication unit 108, a second antenna 109, a first read only memory (ROM) 110, a first random access memory (RAM) 111, and a first control unit 112.

The imaging unit 101 is an imaging module including a lens which forms an image of incident light, an imaging element (a charge-coupled device (CCD), complementary metal-oxide-semiconductor (CMOS) sensor, or the like) which converts the light of the formed image into an electric signal, and an analog-to-digital converter (AD converter) which converts an analog electric signal output from the imaging element into a digital electric signal. The imaging unit 101 images a subject and outputs image data.

The moving-image generation unit 102 generates moving-image data from the image data output from the imaging unit 101. For example, the image data output from the imaging unit 101 is RAW data and the moving-image generation unit 102 generates moving-image data by converting the image data into data suitable for a predetermined moving-image format. The moving-image generation unit 102 may generate moving-image data by performing moving-image compression on the image data output from the imaging unit 101.

The still-image generation unit 103 generates still-image data from the image data output from the imaging unit 101. For example, the image data output from the imaging unit 101 is RAW data and the still-image generation unit 103 generates still-image data by converting the image data into data suitable for a predetermined still-image format. The still-image generation unit 103 may generate still-image data by performing still-image compression on the image data output from the imaging unit 101. The still-image data may be uncompressed data. The number of pixels of the moving-image data may be different from the number of pixels of the still-image data. For example, the number of pixels of the moving-image data may be less than the number of pixels of the still-image data.

The test data generation unit 104 generates test data used for detecting communication quality of each of a plurality of wireless channels. For example, the test data generation unit 104 generates a plurality of pieces of test data constituted of a random code string iterated in a fixed cycle as in a pseudo noise (PN) code. The test data is input from an external device to the endoscope 100 and the input test data may be stored in the first RAM 111 or the like. Therefore, the test data generation unit 104 is not an essential component of the endoscope.

The first operation unit 105 includes a plurality of switches such as a power-supply switch and a release switch. The first operation unit 105 notifies the first control unit 112 of states of the switches and a state change. The first operation unit 105 functions as a release instruction unit which receives an image-recording instruction from the user. By operating the release switch of the first operation unit 105, the user can save still-image data from a point in time at which the release switch is operated. Detailed diagnosis or the like can be performed on the basis of the saved still-image data.

The first wireless communication unit 106 and the second wireless communication unit 108 perform wireless communication with the reception device 200 using any one of the plurality of wireless channels. Frequency bands of the plurality of wireless channels are different. For example, center frequencies of the frequency bands of the plurality of wireless channels are different. Some of the frequency bands of the plurality of wireless channels may overlap.

Each of the first wireless communication unit 106 and the second wireless communication unit 108 is a communication interface (a communication module) including a high-frequency circuit unit necessary for wireless communication, a circuit unit for encoding and decoding, and a buffer memory. The first antenna 107 is connected to the first wireless communication unit 106. The second antenna 109 is connected to the second wireless communication unit 108. In the present embodiment, a wireless local area network (LAN) (Institute of Electrical and Electronics Engineers (IEEE) 802.11) or the like is used as an example of a wireless communication scheme.

The first wireless communication unit 106 performs wireless communication with the reception device 200 via the first antenna 107. For example, the first wireless communication unit 106 sequentially changes the wireless channel to transmit test data to the reception device 200. When the release switch receives the image-recording instruction, the first wireless communication unit 106 transmits still-image data to the reception device 200. More specifically, when the release switch receives the image-recording instruction, the first wireless communication unit 106 transmits the still-image data to the reception device 200 in a predetermined period, i.e., a period in which still-image data of one frame is transmitted. The first wireless communication unit 106 sequentially changes the wireless channel to transmit the test data to the reception device 200 in a period other than the above-mentioned period.

The second wireless communication unit 108 performs wireless communication with the reception device 200 via the second antenna 109. For example, the second wireless communication unit 108 transmits moving-image data to the reception device 200 using a wireless channel different from the wireless channel currently used by the first wireless communication unit 106. The first wireless communication unit 106 and the second wireless communication unit 108 can perform wireless communication in parallel.

In the present embodiment, when the communication quality of the wireless channel used by the second wireless communication unit 108 deteriorates, the wireless channel set in the second wireless communication unit 108 is changed to a wireless channel having better communication quality. On the basis of a communication result of the test data, the wireless channel having the better communication quality is selected. The reception device 200 or the endoscope 100 determines the wireless channel.

The first ROM 110 is a non-volatile memory such as a flash ROM. Program data used for controlling the endoscope 100 and various types of setting information including communication-setting parameters are stored in the first ROM 110. The first RAM 111 is a volatile memory. The first RAM 111 is used as a buffer which temporarily stores image data output from the imaging unit 101, a work area for a calculation by the first control unit 112, and an area in which various types of setting information, etc. are temporarily stored.

The first antenna 107, the second antenna 109, the first ROM 110, and the first RAM 111 are not characteristic components of the endoscope 100.

The first control unit 112 operates according to a program stored in the first ROM 110 and controls the operation of the endoscope 100. For example, the first control unit 112 performs the transmission and reception of the data through the first wireless communication unit 106 and the second wireless communication unit 108. That is, the first control unit 112 causes the first wireless communication unit 106 and the second wireless communication unit 108 to transmit and receive data.

The first control unit 112 functions as the first setting unit which sets the wireless channel determined from the communication quality information about communication quality of the wireless channel used in the transmission of the test data in the second wireless communication unit 108. The first control unit 112 sets the wireless channel determined from the communication quality information in the second wireless communication unit 108 when the communication quality of the wireless channel used by the second wireless communication unit 108 is less than predetermined quality.

The first control unit 112 sets the wireless channel in the first wireless communication unit 106 and sequentially changes the wireless channel set in the first wireless communication unit 106 at a previously designated time interval. The first control unit 112 may include at least any one of the moving-image generation unit 102, the still-image generation unit 103, and the test data generation unit 104.

For example, the function of the first control unit 112 can be implemented as a function of software by causing a computer of the endoscope 100 to read and execute a program including commands defining the operation of the first control unit 112. The program may be provided by a "computer-readable recording medium" such as, for example, a flash memory. The above-mentioned program may be transmitted from a computer storing the program in a storage device or the like to the endoscope 100 via a transmission medium or through transmission waves of the transmission medium and input to the endoscope 100. Here, the transmission medium for transmitting the program is a medium having a function of transmitting information such as a network (a communication network) such as the Internet and a communication circuit (a communication line) such as a telephone line. The above-mentioned program may be a program for implementing some of the above-described functions. Further, the above-mentioned program may be a program, i.e., a so-called differential file (a differential program), capable of implementing the above-mentioned functions in combination with a program already recorded on a computer system.

Figure 3:
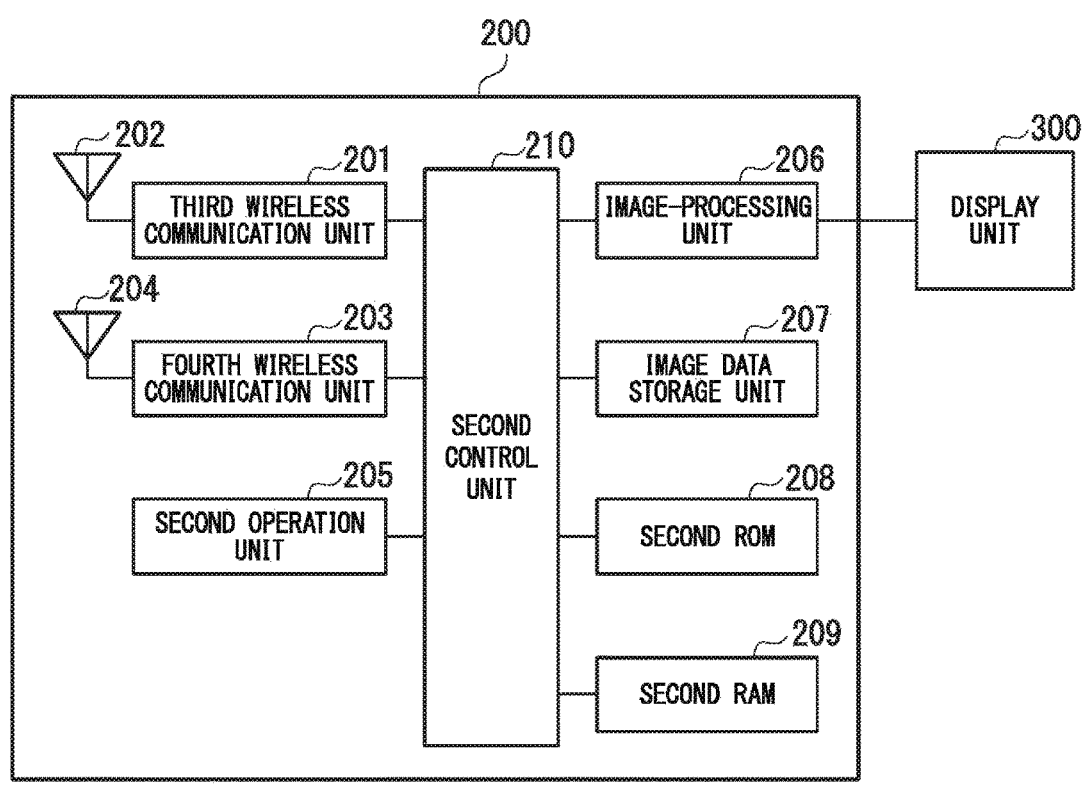
FIG. 3 is a block diagram illustrating a configuration example of a reception device according to an embodiment of the present invention.

FIG. 3 illustrates an electrical configuration example of the reception device 200. As illustrated in FIG. 3, the reception device 200 includes a third wireless communication unit 201, a third antenna 202, a fourth wireless communication unit 203, a fourth antenna 204, a second operation unit 205, an image-processing unit 206, an image data storage unit 207, a second ROM 208, a second RAM 209, and a second control unit 210.

Each of the third wireless communication unit 201 and the fourth wireless communication unit 203 is a communication interface (a communication module) including a high-frequency circuit unit necessary for wireless communication, a circuit unit for encoding and decoding, and a buffer memory. The third antenna 202 is connected to the third wireless communication unit 201. The fourth antenna 204 is connected to the fourth wireless communication unit 203.

The third wireless communication unit 201 uses the wireless channel that is the same as the wireless channel currently used by the first wireless communication unit 106 of the endoscope 100 and performs wireless communication with the endoscope 100 via the third antenna 202. For example, the third wireless communication unit 201 sequentially changes the wireless channel to receive test data used for detecting communication quality of each of the plurality of wireless channels from the endoscope 100. The third wireless communication unit 201 receives still-image data from the endoscope 100. More specifically, when the first operation unit 105 of the endoscope 100 receives an image-recording instruction, the third wireless communication unit 201 receives still-image data from the endoscope 100 in a predetermined period, i.e., in a period in which still-image data of one frame is received. The third wireless communication unit 201 sequentially changes the wireless channel to receive test data from the endoscope 100 in a period other than the above-mentioned period.

The fourth wireless communication unit 203 uses the wireless channel that is the same as the wireless channel used by the second wireless communication unit 108 of the endoscope 100 and performs wireless communication with the endoscope 100 via the fourth antenna 204. For example, the fourth wireless communication unit 203 receives moving-image data from the endoscope 100 using a wireless channel different from the wireless channel used by the third wireless communication unit 201. The third wireless communication unit 201 and the fourth wireless communication unit 203 can perform wireless communication in parallel.

The second operation unit 205 includes a plurality of switches including a power-supply switch, etc. The second operation unit 205 notifies the second control unit 210 of states and state changes of the switches.

The image-processing unit 206 performs image processing on the received moving-image data and converts the moving-image data into display data of a format used in the display of an image. When the moving-image data is compressed, the image-processing unit 206 decompresses the moving-image data and converts the decompressed moving-image data into display data. The image-processing unit 206 outputs the processed display data to the display device 300. The display device 300 displays a moving image on the basis of the display data.

The image-processing unit 206 may perform image processing on the received still-image data and convert the still-image data into display data of a format used in the display of an image. When the still-image data is compressed, the image-processing unit 206 may decompress the still-image data and convert the decompressed still-image data into display data. The display device 300 displays a still image on the basis of the display data.

The image data storage unit 207 is a recording medium such as a hard disk. The image data storage unit 207 stores the received still-image data. The image data storage unit 207 may be a storage device independent of the reception device 200. Therefore, the image data storage unit 207 is not an essential component of the reception device 200.

The second ROM 208 is a non-volatile memory such as a flash ROM. Program data used for controlling the reception device 200 and various types of setting information including a communication-setting parameter are stored in the second ROM 208. The second RAM 209 is a volatile memory. The second RAM 209 is used as a buffer which temporarily stores data received by the third wireless communication unit 201 and the fourth wireless communication unit 203, a work area for calculation by the second control unit 210, and an area in which various types of setting information, etc. are temporarily stored.

The third antenna 202, the fourth antenna 204, the second operation unit 205, the image-processing unit 206, the second ROM 208, and the second RAM 209 are not characteristic components of the reception device 200.

The second control unit 210 operates according to a program stored in the second ROM 208 and controls the operation of the reception device 200. For example, the second control unit 210 performs the transmission and reception of the data through the third wireless communication unit 201 and the fourth wireless communication unit 203. That is, the second control unit 210 causes the third wireless communication unit 201 and the fourth wireless communication unit 203 to transmit and receive data.

The second control unit 210 functions as the second setting unit which sets the wireless channel determined from the communication quality information about communication quality of the wireless channel used in the transmission of the test data in the fourth wireless communication unit 203. The second control unit 210 sets the wireless channel determined from the communication quality information in the fourth wireless communication unit 203 when the communication quality of the wireless channel used by the fourth wireless communication unit 203 is less than predetermined quality.

The second control unit 210 sets the wireless channel in the third wireless communication unit 201 and sequentially changes the wireless channel set in the third wireless communication unit 201 at a previously designated time interval. The second control unit 210 functions as an output unit which outputs the still-image data to the image data storage unit 207. The second control unit 210 may have a function of the image-processing unit 206.

The function of the second control unit 210 can be implemented as a function of software, for example, when a computer of the reception device 200 reads and executes a program including commands defining the operation of the second control unit 210. A method of installing the program may be similar to a method of installing a program for controlling the operation of the first control unit 112 of the endoscope 100.

In the present embodiment, moving-image data and still-image data are transmitted on different wireless channels. Thus, it is possible to perform moving-image transmission more stably than in conventional technology in which the moving-image data and the still-image data are transmitted on the same wireless channel. In the present embodiment, a wireless channel determined from communication quality information about the communication quality of the wireless channel used in the transmission of the test data is set in the second wireless communication unit 108 or the fourth wireless communication unit 203. Thereby, it is possible to use a wireless channel having better communication quality in the moving-image transmission. Thus, it is possible to perform moving-image transmission more stably.

Figure 31:
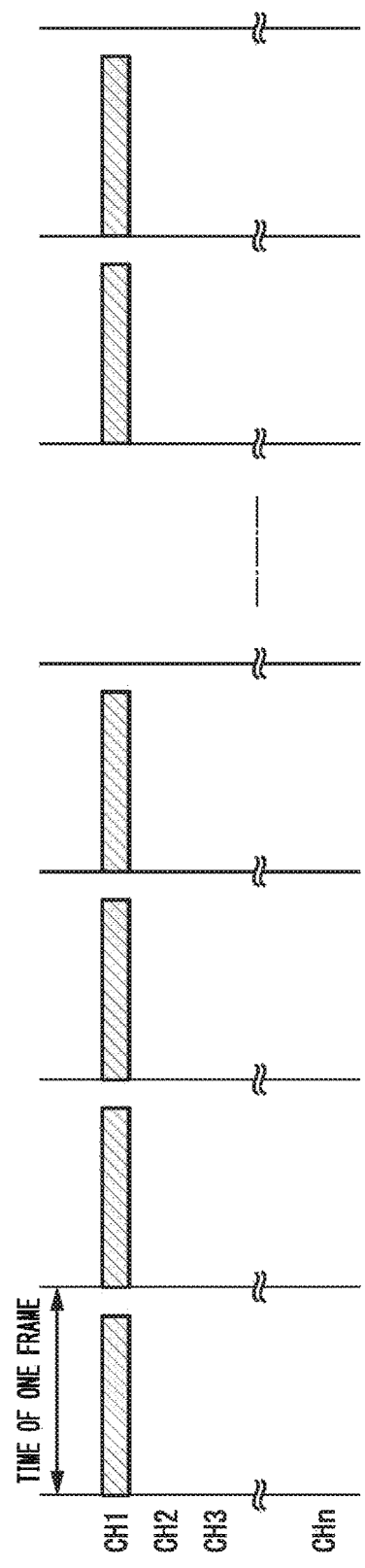
FIG. 31 is a reference diagram illustrating an example of a state in which moving-image data is transmitted in an embodiment of the present invention.

Next, details of the transmission of the moving-image data and the test data will be described. FIG. 31 illustrates an example of a state in which moving-image data is transmitted. The passage of time proceeds to the right in FIG. 31. In FIG. 31, n wireless channels CH1 to CHn are illustrated. n is a natural number greater than or equal to 2. Moving-image data of one frame is transmitted within the time of one frame corresponding to a time in which an image of one frame is displayed. Moving-image data of a plurality of frames is continuously transmitted. The moving-image data is transmitted on a predetermined wireless channel. In FIG. 31, the moving-image data is transmitted on the wireless channel CH1. When the communication quality of the wireless channel CH1 deteriorates, the wireless channel used in the transmission of the moving-image data changes from the wireless channel CH1 to another wireless channel.

Figure 32:
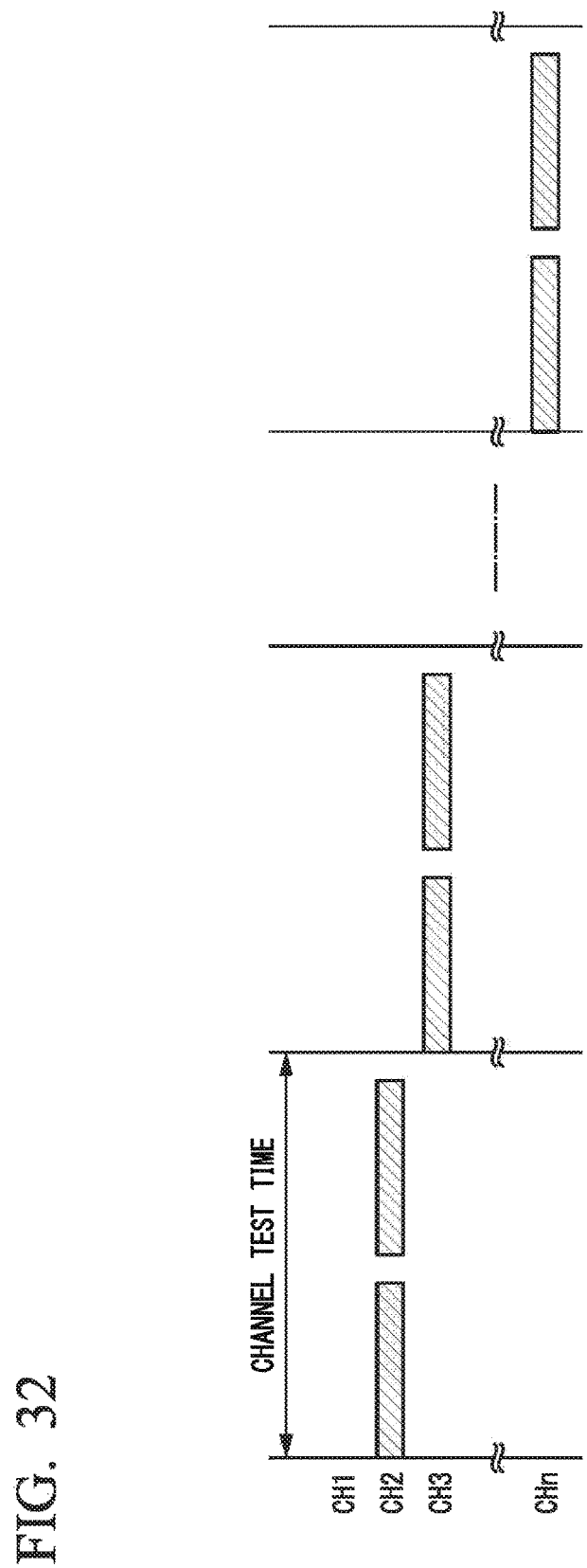
FIG. 32 is a reference diagram illustrating an example of a state in which test data is transmitted in an embodiment of the present invention.

FIG. 32 illustrates an example of a state in which test data is transmitted. The passage of time proceeds to the right in FIG. 32. In FIG. 32, n wireless channels CH1 to CHn are illustrated. n is a natural number greater than or equal to 2. A plurality of pieces of test data are transmitted within a channel test time, which is a predetermined time. In FIG. 32, two pieces of the test data are transmitted within the channel test time. The wireless channel changes every time the channel test time has elapsed. For example, the channel test time is a time greater than or equal to the time of one frame.

Next, operations of the endoscope 100 and the reception device 200 will be described. Hereinafter, first to fourth operation examples will be described. In the first operation example, a wireless channel used in the transmission of the moving-image data is determined by the reception device 200. In the second operation example, a wireless channel used in the transmission of the moving-image data is determined by the endoscope 100. In the third operation example and the fourth operation example, still-image data is transmitted using a fixed wireless channel.

FIRST OPERATION EXAMPLE

Figure 4:
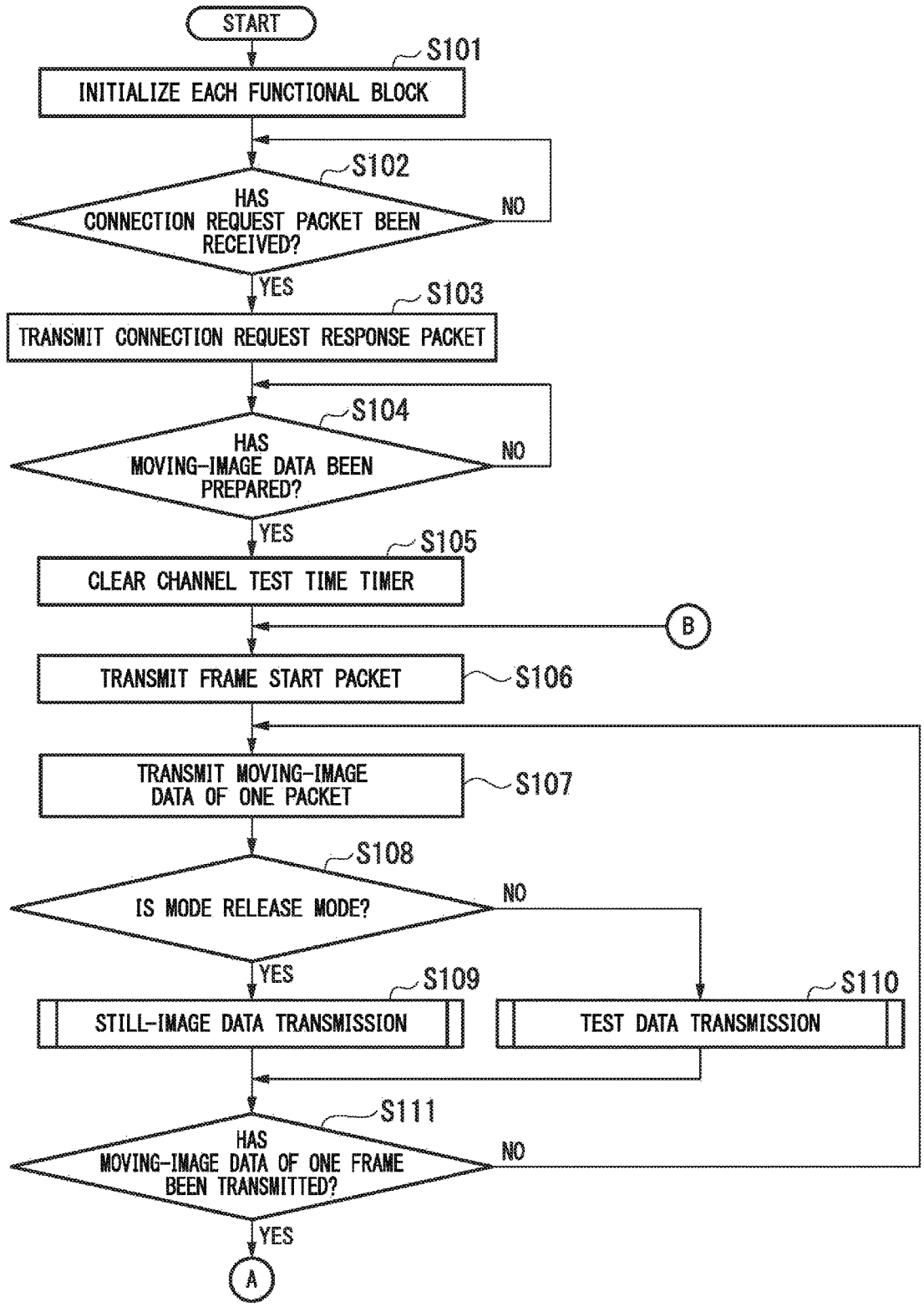
FIG. 4 is a flowchart illustrating a procedure example of an operation of the endoscope according to an embodiment of the present invention.
Figure 5:
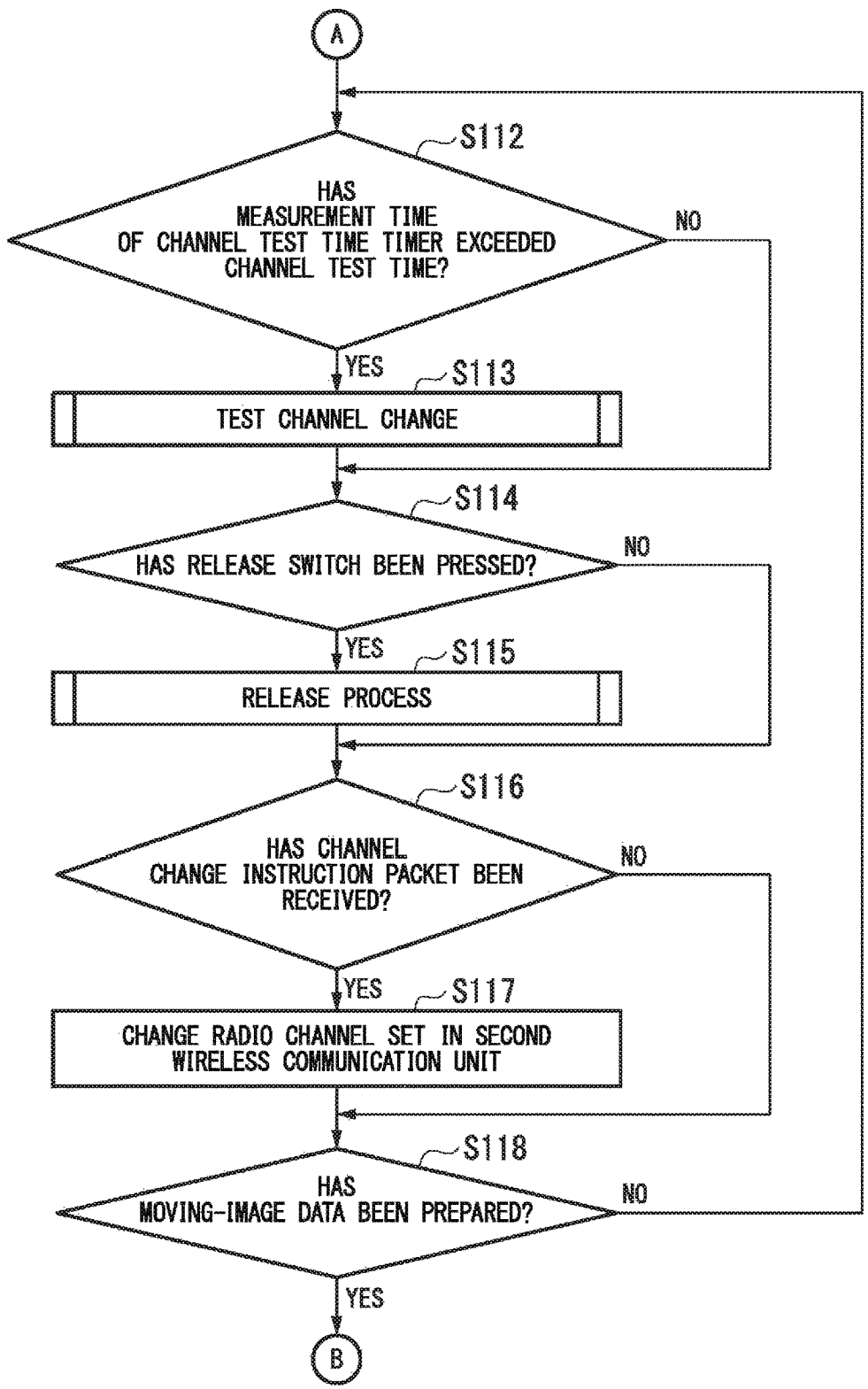
FIG. 5 is a flowchart illustrating a procedure example of an operation of the endoscope according to an embodiment of the present invention.

In the first operation example, the wireless channel used in the transmission of the moving-image data is determined by the reception device 200. FIGS. 4 to 9 illustrate procedure examples of the operation of the endoscope 100 in the first operation example. FIGS. 4 and 5 illustrate main operations of the endoscope 100. FIGS. 6 to 9 illustrate details of the operation illustrated in FIG. 4 or 5.

In the present embodiment, the mode of the endoscope 100 is an auto frequency select (AFS) mode or a release mode. The AFS mode is a mode in which test data is transmitted by the first wireless communication unit 106.

The release mode is a mode in which still-image data is transmitted by the first wireless communication unit 106.

In the present embodiment, the mode of the endoscope 100 is set to the AFS mode immediately after the endoscope 100 is powered on. When the user operates the release switch, the mode of the endoscope 100 is set to the release mode. After the mode of the endoscope 100 is set to the release mode, the mode of the endoscope 100 is set to the AFS mode when the transmission of the still-image data is completed.

When the endoscope 100 is powered on, the first control unit 112 initializes each functional block of the endoscope 100 (step S101). At this time, the first control unit 112 sets a value TEST_CH indicating a wireless channel used in the transmission of test data and a value indicating a wireless channel used in the transmission of moving-image data to an initial value. For example, an initial value of the value TEST_CH is 1. An initial value of the value indicating the wireless channel used in the transmission of the moving-image data is different from the initial value of the value TEST_CH. The first control unit 112 sets wireless channels in the first wireless communication unit 106 and the second wireless communication unit 108 on the basis of the initial values. The first control unit 112 sets a value TEST_NO indicating the number of test data to an initial value. For example, the initial value of the value TEST_NO is 1. The above-mentioned values are stored in the first RAM 111. The first control unit 112 sets a mode of the endoscope 100 to an AFS mode. Information indicating the set mode is stored in the first RAM 111.

In step S101, the imaging unit 101 starts imaging. The moving-image generation unit 102 starts to generate moving-image data. The still-image generation unit 103 starts to generate still-image data. The test data generation unit 104 starts to generate test data.

After each functional block of the endoscope 100 is initialized, the first control unit 112 awaits the reception of a connection request packet transmitted from the reception device 200 (step S102). The connection request packet is a packet for requesting a connection partner of wireless communication to establish a connection for the reception of data. For example, the connection request packet includes a MAC address of the reception device 200. When the connection request packet is transmitted from the reception device 200, the first control unit 112 receives the connection request packet through the first wireless communication unit 106 or the second wireless communication unit 108.

When the connection request packet is received, the first control unit 112 generates a connection request response packet and transmits the generated connection request response packet to the reception device 200 through the first wireless communication unit 106 or the second wireless communication unit 108 (step S103). As a result of this, a wireless connection is established between the endoscope 100 and the reception device 200. The connection request response packet is a response to the connection request packet.

After the connection request response packet is transmitted, the first control unit 112 detects the state of the moving-image generation unit 102 and determines whether moving-image data is prepared (step S104). When no moving-image data is prepared, the process of step S104 is performed again.

When the moving-image data is prepared, the first control unit 112 clears a channel test time timer (step S105).

Thereby, the time measured by the channel test time timer is initialized. The channel test time timer is a timer for measuring the channel test time.

After the channel test time timer is cleared, the first control unit 112 generates a frame start packet and transmits the generated frame start packet to the reception device 200 through the first wireless communication unit 106 or the second wireless communication unit 108 (step S106). The frame start packet is a packet for providing a notification of the start of the time of one frame.

After the frame start packet is transmitted, the first control unit 112 transmits moving-image data of one packet among the moving-image data generated by the moving-image generation unit 102 to the reception device 200 through the second wireless communication unit 108 (step S107). That is, the first control unit 112 transmits moving-image data generated from the image data output from the imaging unit 101 to the reception device 200 through the second wireless communication unit 108 using a wireless channel different from a wireless channel currently used by the first wireless communication unit 106.

After the moving-image data is transmitted, the first control unit 112 determines whether the mode of the endoscope 100 is the release mode on the basis of information indicating the mode of the endoscope 100 (step S108). The information indicating the mode of the endoscope 100 is stored in the first RAM 111.

When the mode of the endoscope 100 is the release mode, still-image data is transmitted (step S109). Details of step S109 will be described below.

When the mode of the endoscope 100 is not the release mode, i.e., when the mode of the endoscope 100 is the AFS mode, test data is transmitted (step S110). Details of step S110 will be described below.

After the process of step S109 or S110 is performed, the first control unit 112 determines whether moving-image data of one frame is transmitted (step S111). When the transmission of the moving-image data of the one frame is not completed, the process of step S107 is performed again.

When the transmission of the moving-image data of the one frame is completed, the first control unit 112 detects a time measured by the channel test time timer and determines whether the measured time exceeds the channel test time (step S112).

When the time measured by the channel test time timer exceeds the channel test time, the test channel is changed (step S113). The test channel is a wireless channel used in the transmission of the test data. Details of step S113 will be described below. When the time measured by the channel test time timer does not exceed the channel test time, the test channel is not changed.

Next, the first control unit 112 detects the state of the first operation unit 105 and determines whether the release switch is pressed (step S114). When the release switch is pressed, a release process is performed (step S115). The release process is a process for transmitting still-image data. Details of step S115 will be described below. When no release switch is pressed, no release process is performed.

Next, the first control unit 112 awaits the reception of a channel change instruction packet transmitted from the reception device 200 (step S116). The channel change instruction packet is a packet for issuing an instruction for changing a wireless channel used in the transmission of moving-image data. The channel change instruction packet includes wireless channel information indicating a wireless channel determined from communication quality information about communication quality of a wireless channel used in the transmission of test data. When the channel change instruction packet is transmitted from the reception device 200, the first control unit 112 receives the channel change instruction packet through the first wireless communication unit 106 or the second wireless communication unit 108.

When the channel change instruction packet is received, the first control unit 112 sets a wireless channel indicated by wireless channel information included in the channel change instruction packet in the second wireless communication unit 108 (step S117). That is, the first control unit 112 sets a wireless channel determined from the communication quality information about the communication quality of the wireless channel used in the transmission of test data in the second wireless communication unit 108. Thereby, the wireless channel set in the second wireless communication unit 108 is changed. When no channel change instruction packet is received, the wireless channel to be used by the second wireless communication unit 108 is not changed.

Next, the first control unit 112 detects the state of the moving-image generation unit 102 and determines whether moving-image data is prepared (step S118). When no moving-image data is prepared, the process of step S112 is performed again. When the moving-image data is prepared, the process of step S106 is performed again.

Figure 6:
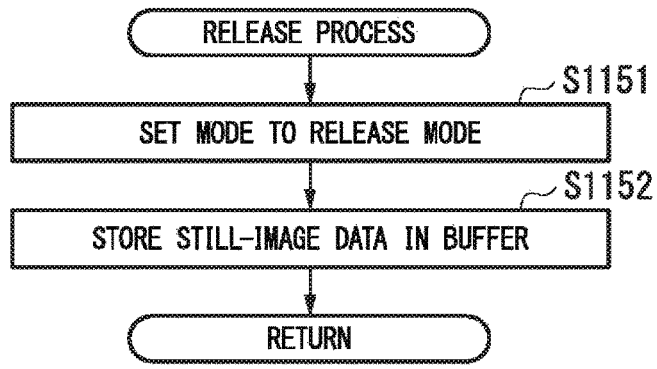
FIG. 6 is a flowchart illustrating a procedure example of an operation of the endoscope according to an embodiment of the present invention.

FIG. 6 illustrates details of step S115. Because the release switch is pressed, the first control unit 112 sets the mode of the endoscope 100 to the release mode (step S1151). Information indicating the set mode is stored in the first RAM 111.

After the mode of the endoscope 100 is set to the release mode, the first control unit 112 waits for still-image data to be generated by the still-image generation unit 103. After the still-image data is generated by the still-image generation unit 103, the first control unit 112 stores the generated still-image data in a buffer provided in the first RAM 111 (step S1152). Thereby, still-image data generated at the timing designated according to an operation of the release switch by the user is stored in the buffer. The still-image generation unit 103 may stop an operation when the release switch is not operated and the still-image generation unit 103 may start to generate still-image data when the release switch is operated. After the still-image data is stored in the buffer, the process of step S115 ends.

Figure 7:
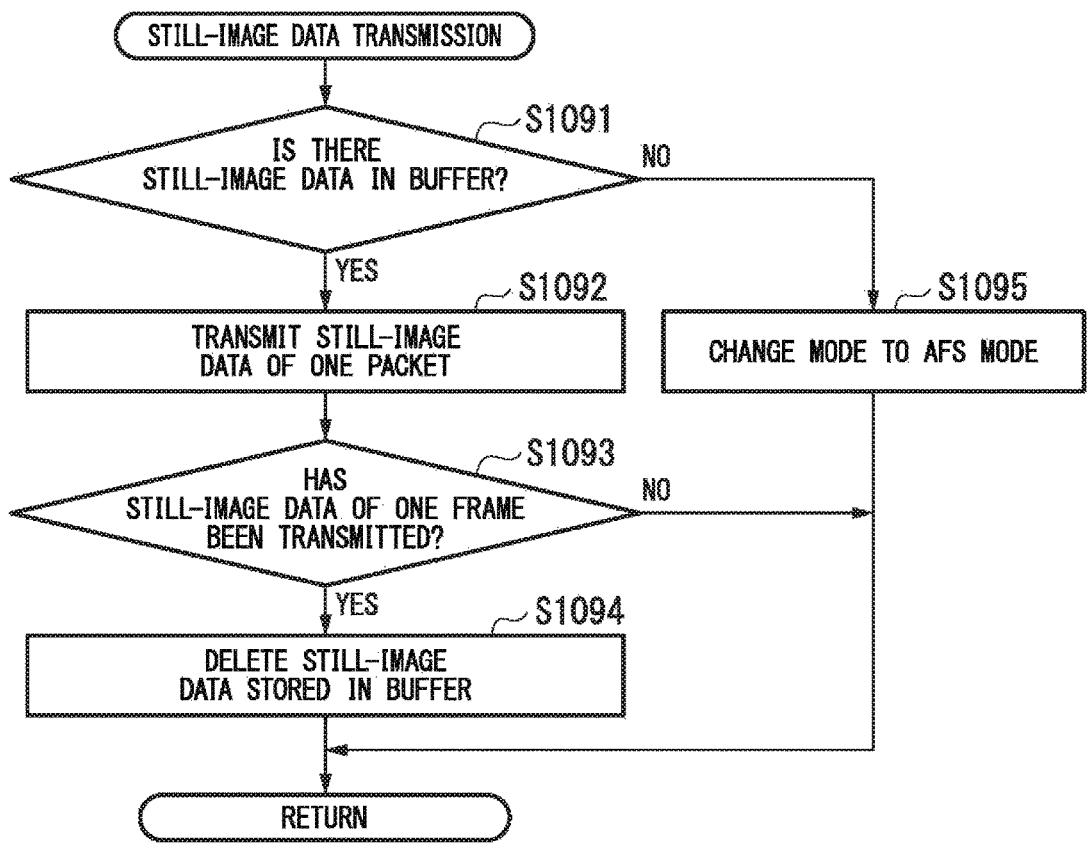
FIG. 7 is a flowchart illustrating a procedure example of an operation of the endoscope according to an embodiment of the present invention.

FIG. 7 illustrates details of step S109. The first control unit 112 determines whether the still-image data is stored in the buffer provided in the first RAM 111 (step S1091). Still-image data generated by the still-image generation unit 103 is stored in the buffer.

When the still-image data is stored in the buffer, the first control unit 112 transmits still-image data of one frame among the still-image data generated by the still-image generation unit 103 to the reception device 200 through the first wireless communication unit 106 (step S1092). That is, when an image-recording instruction is received from the user, the first control unit 112 transmits the still-image data generated from the image data output from the imaging unit 101 to the reception device 200 through the first wireless communication unit 106. Thus, when the image-recording instruction is received from the user, the first control unit 112 transmits the still-image data instead of test data to the reception device 200 through the first wireless communication unit 106.

After the still-image data is transmitted, the first control unit 112 determines whether still-image data of one frame is transmitted (step S1093). When the transmission of the still-image data of the one frame is not completed, the process of step S109 ends.

When the transmission of the still-image data of the one frame is completed, the first control unit 112 deletes the still-image data stored in the buffer provided in the first RAM 111 (step S1094). After the still-image data is deleted, the process of step S109 ends.

When no still-image data is stored in the buffer in step S1091, the first control unit 112 sets the mode of the endoscope 100 to the AFS mode (step S1095). Information indicating the set mode is stored in the first RAM 111. After the node of the endoscope 100 is set to the AFS mode, the process of step S109 ends.

Figure 8:
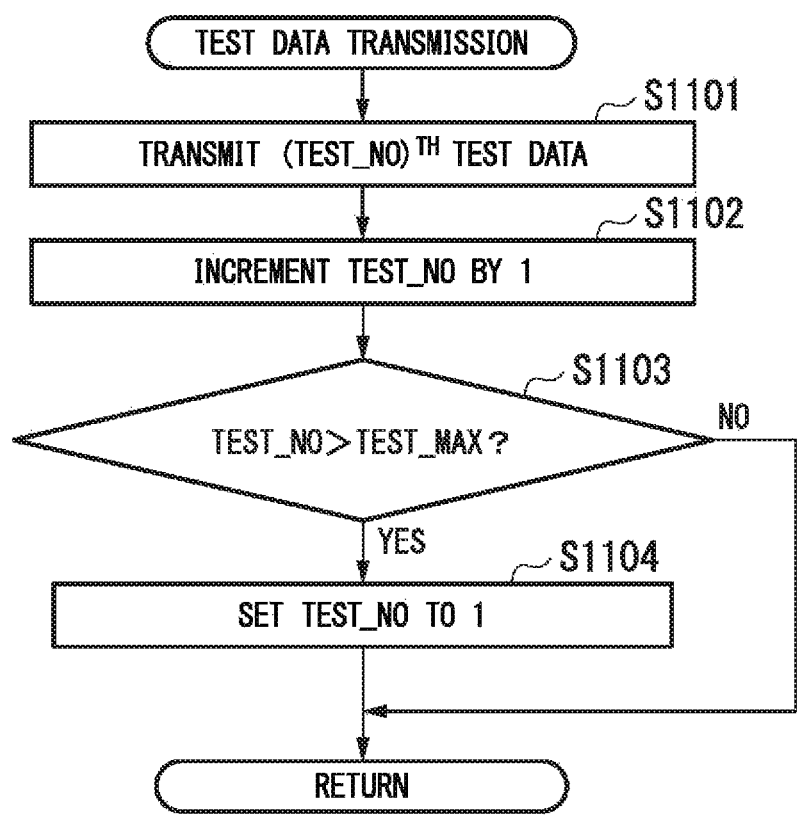
FIG. 8 is a flowchart illustrating a procedure example of an operation of the endoscope according to an embodiment of the present invention.

FIG. 8 illustrates details of step S110. The first control unit 112 transmits test data having the number of TEST_NO generated by the test data generation unit 104 to the reception device 200 through the first wireless communication unit 106 (step S1101). For example, one piece of test data is divided into a plurality of pieces of data and a plurality of packets including the divided data are transmitted.

After the test data is transmitted, the first control unit 112 increments the value TEST_NO indicating the number of the test data by 1 (step S1102). After the value TEST_NO is incremented by 1, the first control unit 112 determines whether the value TEST_NO is greater than a value TEST_MAX (step S1103). The value TEST_MAX is a maximum value of the number of the test data. The value TEST_MAX is pre-stored in the first RAM 111.

When the value TEST_NO is less than or equal to the value TEST_MAX, the process of step S110 ends. When the value TEST_NO is greater than the value TEST_MAX, the first control unit 112 sets the value TEST_NO to 1, which is the initial value (step S1104). When the value TEST_NO is set to 1, the process of step S110 ends.

Figure 9:
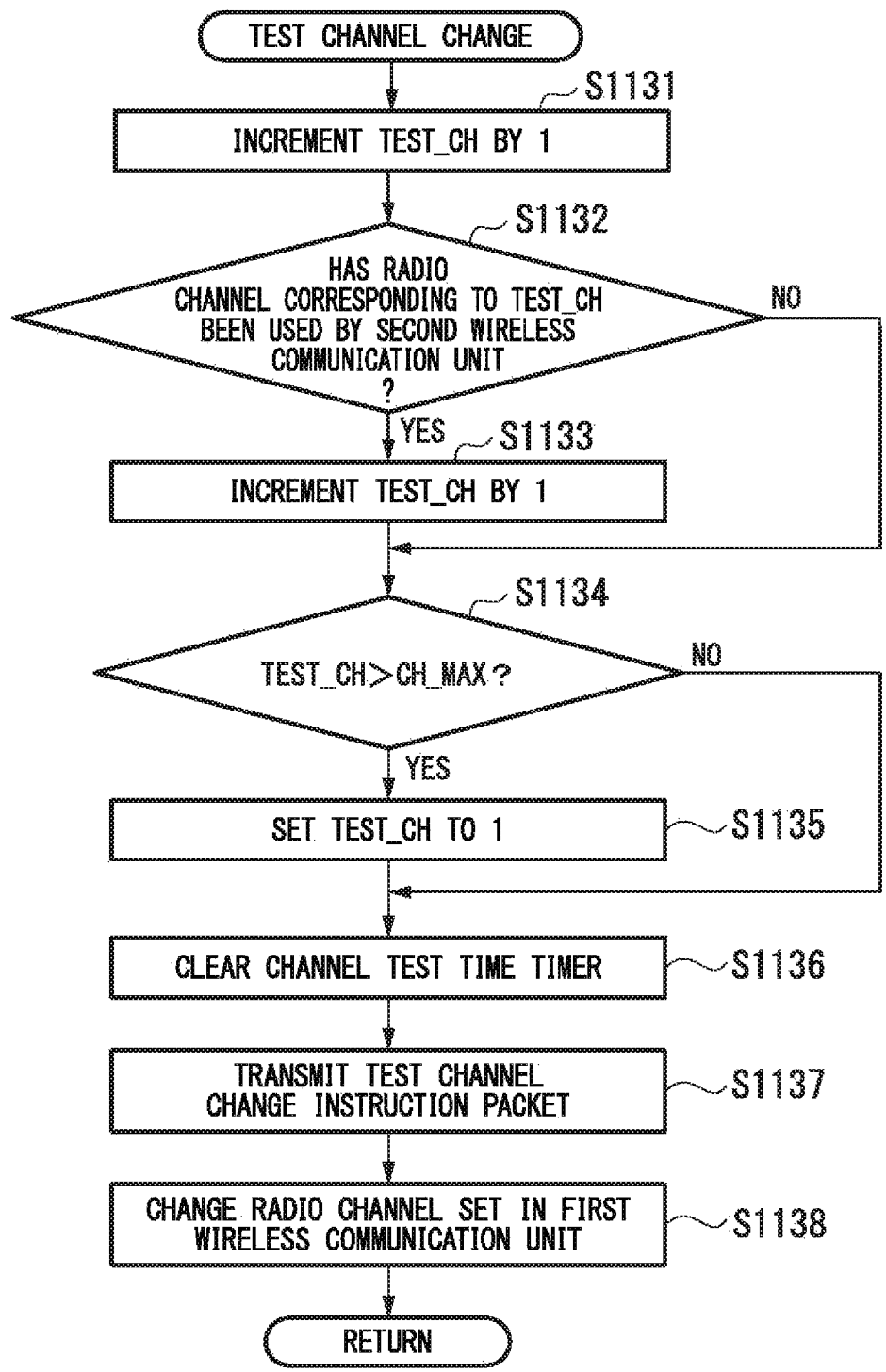
FIG. 9 is a flowchart illustrating a procedure example of an operation of the endoscope according to an embodiment of the present invention.

FIG. 9 illustrates details of step S113. The first control unit 112 increments the value TEST_CH indicating the wireless channel used in the transmission of the test data by 1 (step S1131).

After the value TEST_CH is incremented by 1, the first control unit 112 determines whether a wireless channel corresponding to the value TEST_CH is used by the second wireless communication unit 108 (step S1132). At this time, the first control unit 112 makes a determination by comparing the value TEST_CH with the value indicating the wireless channel used by the second wireless communication unit 108, i.e., the wireless channel used in the transmission of the moving-image data. When the two values are the same, the wireless channel corresponding to the value TEST_CH is determined to be used by the second wireless communication unit 108. When the two values are different, the wireless channel corresponding to the value TEST_CH is determined to be unused by the second wireless communication unit 108.

When the wireless channel corresponding to the value TEST_CH is used by the second wireless communication unit 108, the first control unit 112 increments the value TEST_CH by 1 (step S1133). Thereby, the wireless channel currently used by the first wireless communication unit 106 and the wireless channel used by the second wireless communication unit 108 do not overlap. When the wireless channel corresponding to the value TEST_CH is unused by the second wireless communication unit 108, the value TEST_CH is not incremented.

Next, the first control unit 112 determines whether the value TEST_CH is greater than the value CH_MAX (step S1134). The value CH_MAX is a maximum value of the number of wireless channels. The value CH_MAX is pre-stored in the first RAM 111.

When the value TEST_CH is greater than the value CH_MAX, the first control unit 112 sets the value TEST_CH to 1, which is an initial value (step S1135). When the value TEST_CH is less than or equal to the value CH_MAX, the value TEST_CH is not changed.

Next, the first control unit 112 clears a channel test time timer (step S1136). Thereby, a time measured by the channel test time timer is initialized.

After the channel test time timer is cleared, the first control unit 112 generates a test channel change instruction packet and transmits the generated test channel change instruction packet to the reception device 200 through the first wireless communication unit 106 or the second wireless communication unit 108 (step S1137). The test channel change instruction packet is a packet for issuing an instruction for setting a wireless channel to be used in the transmission of the test data. The test channel change instruction packet includes wireless channel information indicating a wireless channel used in the transmission of the test data. A value indicated by the wireless channel information is the same as the value TEST_CH.

After the test channel change instruction packet is transmitted, the first control unit 112 sets the wireless channel indicated by the value TEST_CH in the first wireless communication unit 106 (step S1138). Thereby, the wireless channel set in the first wireless communication unit 106 is changed. After the wireless channel is changed, the process of step S113 ends.

The process of step S112 and the process of step S113 are performed both while the test data is transmitted and while the still-image data is transmitted. When the time measured by the channel test time timer exceeds the channel test time during the transmission of the test data, the wireless channel is changed in the process of step S113. That is, the first control unit 112 sequentially changes the wireless channel at an interval of a preset time, i.e., a channel test time, to transmit the test data used for detecting communication quality of each of a plurality of wireless channels to the reception device 200 through the first wireless communication unit 106.

Likewise, when the time measured by the channel test time timer exceeds the channel test time during the transmission of still-image data of one frame, the wireless channel is changed in the process of step S113. That is, when the release switch receives a still-image-recording instruction from the user, the first control unit 112 sequentially changes the wireless channel of the first wireless communication unit 106 at an interval of a preset channel test time to transmit still-image data to the reception device 200 through the first wireless communication unit 106.

As described above, it is possible to perform the transmission of the still-image data and the acquisition of information about communication quality of the wireless channel used in the transmission of the still-image data in parallel by sequentially changing the wireless channel to transmit still-image data. In this case, it is possible to use the still-image data as test data. That is, the still-image data is equivalent to the test data in the first operation example.

Figure 33A:
FIG. 33A is a reference diagram illustrating a configuration example of a packet of test data in an embodiment of the present invention.
Figure 33B:
FIG. 33B is a reference diagram illustrating a configuration example of a packet of still-image data in an embodiment of the present invention.

FIGS. 33A and 33B illustrate configuration examples of a packet of test data and a packet of still-image data. FIG. 33A illustrates the configuration of a packet PCK1, which is the packet of the test data. A data identifier is stored in a field of a header of the packet PCK1. The data identifier indicates either the test data or the still-image data. The data identifier of the packet PCK1 indicates the test data. In the packet PCK1, the test data is stored in a field subsequent to the field of the header. The test data includes a test data number and a main body of the test data.

FIG. 33B illustrates the configuration of the packet PCK2, which is the packet of the still-image data. A data identifier is stored in a field of a header of the packet PCK2. The data identifier of the packet PCK2 indicates still-image data. In the packet PCK2, the still-image data is stored in a field subsequent to the field of the header. The still-image data includes a still-image data number, an end mark, and a main body of the still-image data. The still-image data number indicates the order of data when still-image data of one frame is divided into data stored in each packet. The end mark indicates the last transmitted packet among a plurality of packets for transmitting the still-image data of the one frame.

The first control unit 112 of the endoscope 100 transmits the packet PCK1 or PCK2 to the reception device 200 through the first wireless communication unit 106. Thereby, the first control unit 112 can transmit information for identifying the test data and the still-image data, i.e., a data identifier, to the reception device 200 through the first wireless communication unit 106.

The second control unit 210 of the reception device 200 receives the packet PCK1 or PCK2 from the endoscope 100 through the third wireless communication unit 201. Thereby, the second control unit 210 can receive information for identifying the test data and the still-image data, i.e., data identifiers, from the endoscope 100 through the third wireless communication unit 201. The second control unit 210 performs a process related to the test data or the still-image data included in the packet PCK1 or PCK2 according to the received data identifiers. Thereby, the reception device 200 can perform a process according to a type of data.

Details of the processes illustrated in FIGS. 4 to 9 can be appropriately changed.

Figure 10:
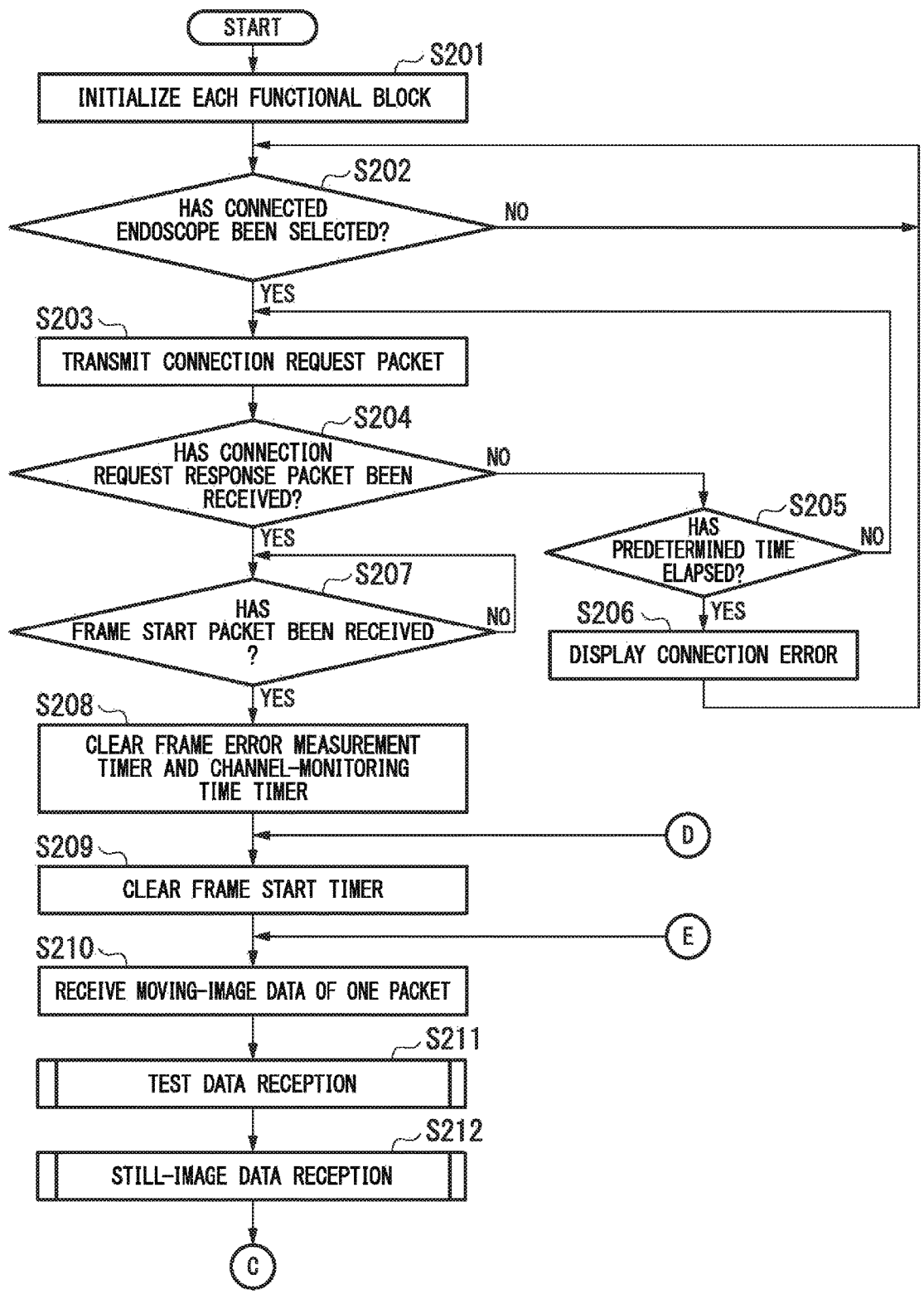
FIG. 10 is a flowchart illustrating a procedure example of an operation of the reception device according to an embodiment of the present invention.
Figure 11:
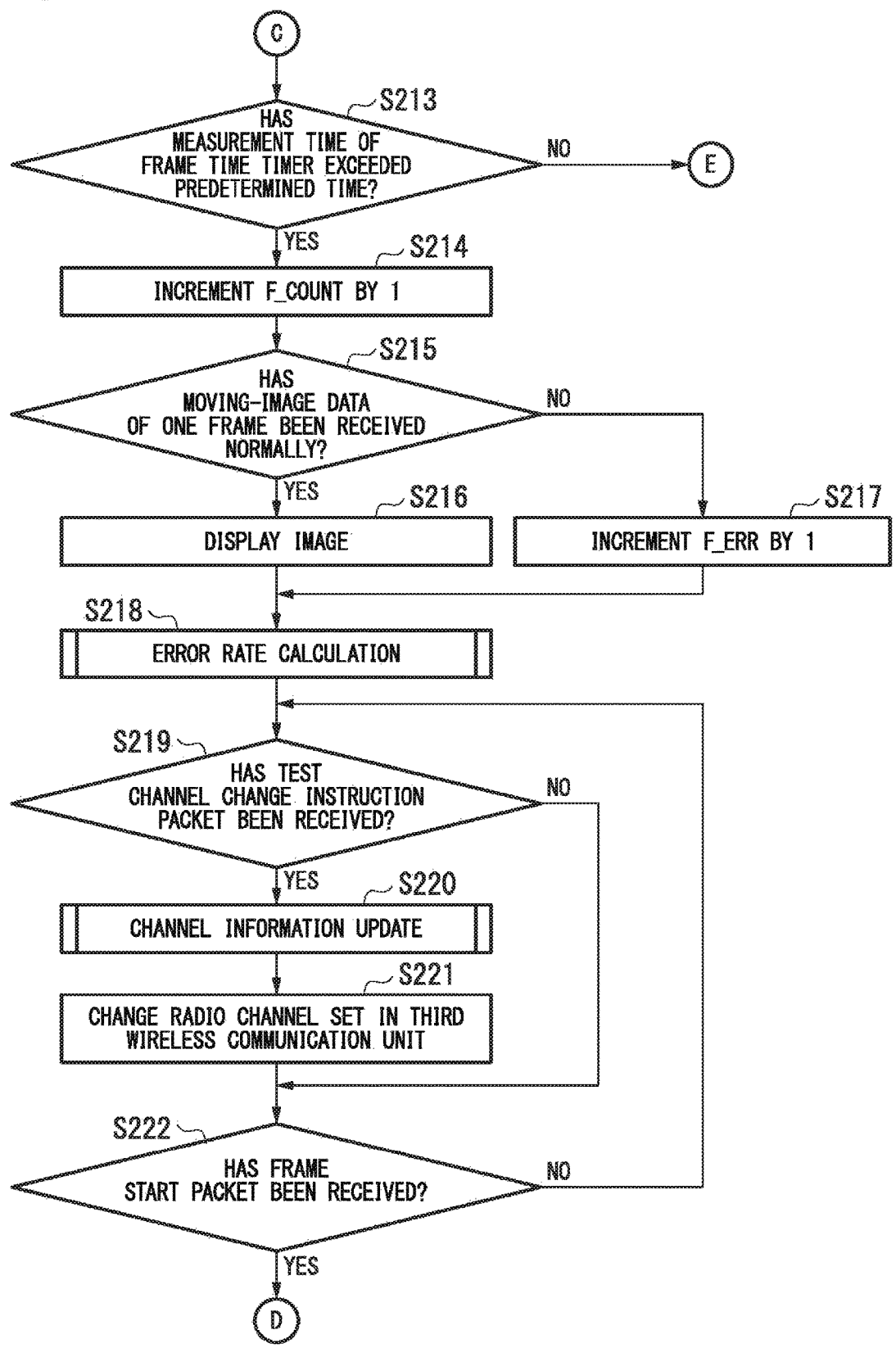
FIG. 11 is a flowchart illustrating a procedure example of an operation of the reception device according to an embodiment of the present invention.

FIGS. 10 to 15 illustrate procedure examples of the operation of the reception device 200 in the first operation example. FIGS. 10 and 11 illustrate main operations of the reception device 200. FIGS. 12 to 15 illustrate details of the operation illustrated in FIG. 10 or 11.

When the reception device 200 is powered on, the second control unit 210 initializes each functional block of the reception device 200 (step S201). At this time, the second control unit 210 sets the value TEST_CH indicating the wireless channel used in the reception of the test data and the a value indicating wireless channel used in the reception of the moving-image data to initial values. For example, the initial value of the value TEST_CH is 1. The initial value of the value indicating the wireless channel used in the transmission of the moving-image data is a value different from the initial value of the value TEST_CH. The second control unit 210 sets the wireless channels in the third wireless communication unit 201 and the fourth wireless communication unit 203 on the basis of these initial values. The second control unit 210 sets a value F_COUNT indicating a number of a frame and a value F_ERR indicating the number of errors in the transmission of the moving-image data to initial values. For example, these initial values are 0. The above-mentioned values are stored in the second RAM 209.

The second control unit 210 sets a value D_AMOUNT[n] indicating an amount of data received for each wireless channel and a value CH_STATUS[n] indicating a communication rate for each wireless channel to initial values. n indicates the number of wireless channels. The value D_AMOUNT[n] indicates an amount of data received on an $n^{th}$ wireless channel. The value CH_STATUS[n] indicates a communication rate of the $n^{th}$ wireless channel. For example, these initial values are 0. The value D_AMOUNT[n] and the value CH_STATUS[n] are stored in the second RAM 209.

After each functional block of the endoscope 100 is initialized, the second control unit 210 detects content of an operation by the user on the basis of a signal from the second operation unit 205 and waits for the user to select the endoscope 100 of a connection partner (step S202). Information about the endoscope 100 selectable as the connection partner is previously stored in the second ROM 208.

When the user selects the endoscope 100 of the connection partner, the second control unit 210 identifies the endoscope 100 selected as the connection partner on the basis of the signal from the second operation unit 205. The second control unit 210 generates a connection request packet and transmits the generated connection request packet to the endoscope 100 selected as the connection partner by the third wireless communication unit 201 or the fourth wireless communication unit 203 (step S203).

After the connection request packet is transmitted, the second control unit 210 awaits the reception of a connection request response packet transmitted from the endoscope 100 (step S204). When the connection request response packet is transmitted from the endoscope 100, the second control unit 210 receives the connection request response packet through the third wireless communication unit 201 or the fourth wireless communication unit 203.

When no connection request response packet is received, the second control unit 210 determines whether a time that has elapsed from a point in time at which the connection request packet was transmitted exceeds a predetermined time (step S205). When the time that has elapsed from the point in time at which the connection request packet was transmitted does not exceed the predetermined time, the process of step S203 is performed again. When the time that has elapsed from the point in time at which the connection request packet was transmitted exceeds the predetermined time, the second control unit 210 causes the display device 300 to display a connection error (step S206). After the connection error is displayed, the process of step S202 is performed again.

When the connection request response packet is received, the second control unit 210 awaits the reception of a frame start packet transmitted from the endoscope 100 (step S207). When the frame start packet is transmitted from the endoscope 100, the second control unit 210 receives the frame start packet through the third wireless communication unit 201 or the fourth wireless communication unit 203.

After the frame start packet is received, the second control unit 210 clears a frame error measurement timer and a channel-monitoring time timer (step S208). Thereby, a time measured by the frame error measurement timer and a time measured by the channel-monitoring time timer are initialized. The frame error measurement timer is a timer for measuring a time for which the number of occurrences of an error of the moving-image data is detected. The channel-monitoring time timer is a timer for measuring a channel motoring time. The channel-monitoring time is a time for which the state of the wireless channel is monitored for measurement of the communication rate.

After the frame error measurement timer and the channel-monitoring time timer are cleared, the second control unit 210 clears the frame time timer (step S209). Thereby, the time measured by the frame time timer is initialized. The frame time timer is a timer for measuring the time of one frame.

After the frame time timer is cleared, the second control unit 210 awaits the reception of moving-image data of one frame transmitted from the endoscope 100. When the moving-image data of the one frame is transmitted from the endoscope 100, the second control unit 210 receives moving-image data through the fourth wireless communication unit 203 (step S210). That is, the second control unit 210 receives the moving-image data from the endoscope 100 through the fourth wireless communication unit 203 using a wireless channel different from the wireless channel used by the third wireless communication unit 201.

After the moving-image data is received, a process related to the reception of the test data is performed (step S211). Details of the process of step S211 will be described below.

After the process related to the reception of the test data is performed, a process related to the reception of still-image data is performed (step S212). Details of the process of step S212 will be described below. The order in which the process of step S211 and the process of step S212 are performed may be reversed.

After the process related to the reception of the still-image data is performed, the second control unit 210 determines whether the time measured by the frame time timer exceeds a predetermined time, i.e., the time of one frame (step S213). When the time measured by the frame time timer does not exceed the time of one frame, the process of step S210 is performed again.

When the time measured by the frame time timer exceeds the time of one frame, the second control unit 210 increments the value F_COUNT by 1 (step S214). After the value F_COUNT is incremented by 1, the second control unit 210 determines whether moving-image data of one frame is received normally (step S215). When the reception of the moving-image data of the one frame is completed within the time of one frame, the moving-image data of the one frame is determined to be received normally. When the number of retransmissions increases and therefore the reception of the moving-image data of the one frame is not completed within the time of one frame, it is determined that the moving-image data of the one frame is not received normally.

When the moving-image data of the one frame is received normally, the second control unit 210 performs image processing of the moving-image data through the image-processing unit 206 and displays an image of one frame constituting a moving image through the display device 300 (step S216). That is, the second control unit 210 displays an image based on the received moving-image data through the display device 300. When the moving-image data of the one frame is not received normally, the second control unit 210 increments the value F_ERR by 1 (step S217).

After the image is displayed or after the value F_ERR is incremented by 1, an error rate of the moving-image data of the one frame is calculated (step S218). Details of step S218 will be described below.

After the error rate of the moving-image data of the one frame is calculated, the second control unit 210 awaits the reception of a test channel change instruction packet transmitted from the endoscope 100 (step S219). When the test channel change instruction packet is transmitted from the endoscope 100, the second control unit 210 receives the test channel change instruction packet through the third wireless communication unit 201 or the fourth wireless communication unit 203.

When the test channel change instruction packet is received, information about the wireless channel is changed (step S220). Details of step S220 will be described below.

After the information about the wireless channel is updated, the second control unit 210 changes the wireless channel set in the third wireless communication unit 201 on the basis of a result of processing of step S220 (step S221). Details of step S221 will be described below. When no test channel change instruction packet is received, the process of S220 and the process of step S221 are not performed.

Next, the second control unit 210 awaits the reception of a frame start packet transmitted from the endoscope 100 (step S222). When the frame start packet is transmitted from the endoscope 100, the second control unit 210 receives the frame start packet through the third wireless communication unit 201 or the fourth wireless communication unit 203.

When no frame start packet is received, the process of step S219 is performed again. When the frame start packet is received, the process of step S209 is performed again.

Figure 12:
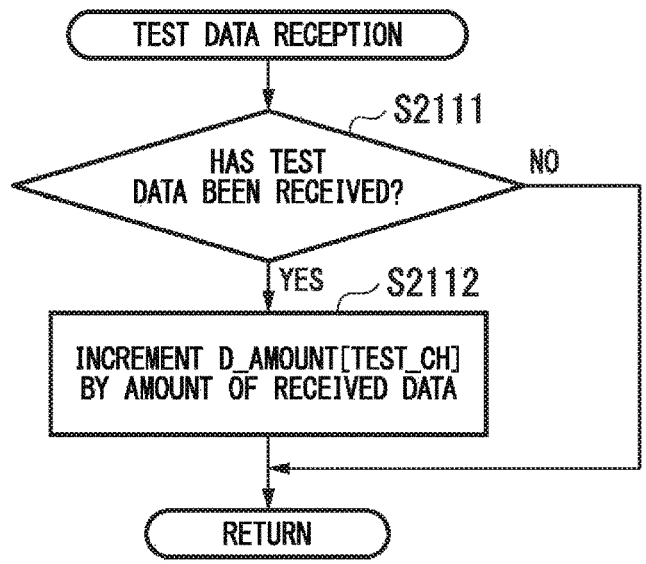
FIG. 12 is a flowchart illustrating a procedure example of an operation of the reception device according to an embodiment of the present invention.

FIG. 12 illustrates details of step S211. The second control unit 210 awaits the reception of the test data transmitted from the endoscope 100 (step S2111). When the test data is transmitted from the endoscope 100, the second control unit 210 receives the test data through the third wireless communication unit 201.

As described above, the first wireless communication unit 106 of the endoscope 100 sequentially changes the wireless channel to transmit the test data to the reception device 200. Thus, the second control unit 210 of the reception device 200 sequentially changes the wireless channel to receive the test data through the third wireless communication unit 201.

When the test data is received, the second control unit 210 increments the value D_AMOUNT[TEST_CH] by an amount of received data (step S2112). The amount of received data may be the number of received packets. When no test data is received, the value D_AMOUNT[TEST_CH] is not updated. The process of step S211 ends according to the above process.

Figure 13:
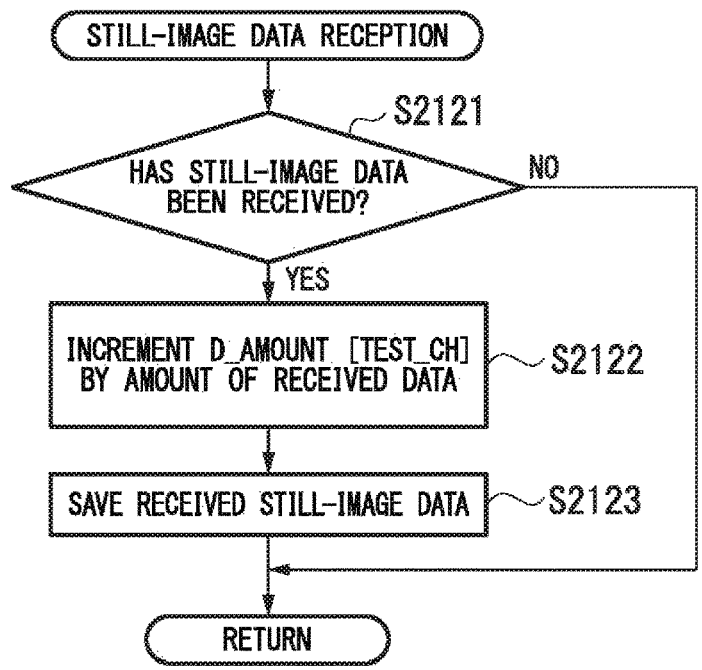
FIG. 13 is a flowchart illustrating a procedure example of an operation of the reception device according to an embodiment of the present invention.

FIG. 13 illustrates details of step S212. The second control unit 210 awaits the reception of still-image data transmitted from the endoscope 100 (step S2121). When the still-image data is transmitted from the endoscope 100, the second control unit 210 receives the still-image data through the third wireless communication unit 201.

As described above, the first wireless communication unit 106 of the endoscope 100 sequentially changes the wireless channel to transmit the still-image data to the reception device 200. Thus, the second control unit 210 of the reception device 200 sequentially changes the wireless channel to receive the still-image data through the third wireless communication unit 201.

When the still-image data is received, the second control unit 210 increments the value D_AMOUNT[TEST_CH] by an amount of received data (step S2122). The amount of received data may be the number of received packets. Because the still-image data is also used as the test data, a communication result of the still-image data is reflected in the value D_AMOUNT[TEST_CH]. When the still-image is not used as the test data, it is unnecessary to perform the process of step S2122. When no still-image data is received, the value D_AMOUNT[TEST_CH] is not updated.

After the value D_AMOUNT[TEST_CH] is updated, the second control unit 210 saves the received still-image data in the image data storage unit 207 (step S2123).

After the still-image data is saved, the process of step S212 ends.

Figure 14:
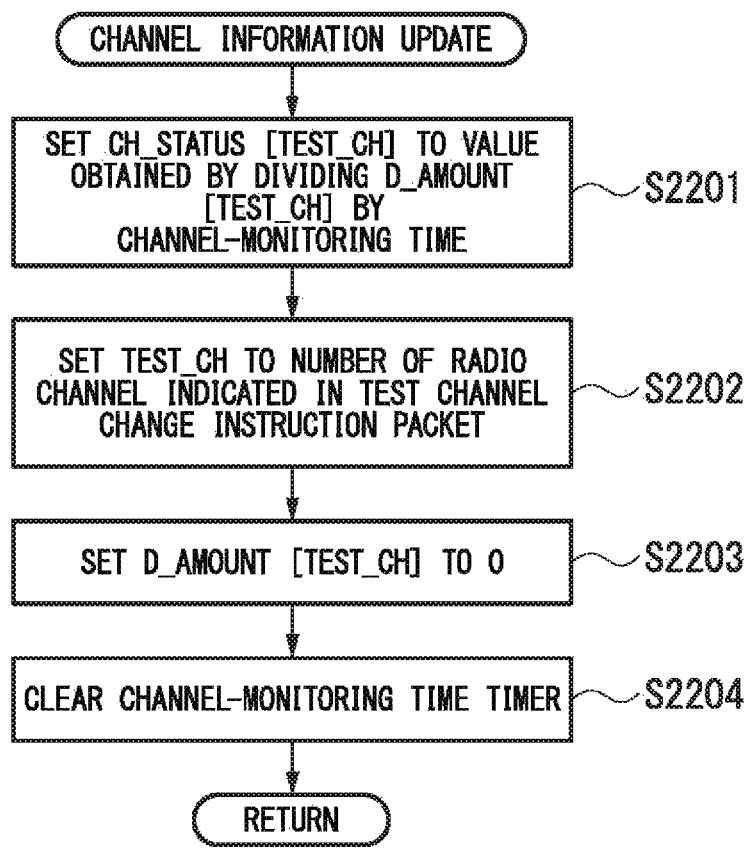
FIG. 14 is a flowchart illustrating a procedure example of an operation of the reception device according to an embodiment of the present invention.

FIG. 14 illustrates details of step S220. The second control unit 210 sets the value CH_STATUS[TEST_CH] to a value obtained by dividing the value D_AMOUNT[TEST_CH] by a channel-monitoring time (step S2201). As described above, the value CH_STATUS[TEST_CH] indicates a communication rate of a TEST-CH$^{th}$ wireless channel. That is, the value CH_STATUS[TEST_CH] is communication quality information about communication quality of a wireless channel on which test data is received. The channel-monitoring time is a time measured by the channel-monitoring time timer.

After the value CH_STATUS[TEST_CH] is set, the second control unit 210 sets the value TEST_CH to the number of a wireless channel indicated by the test channel change instruction packet (step S2202). As described above, the test channel change instruction packet includes wireless channel information indicating a wireless channel used in the transmission of test data. In step S2202, the second control unit 210 sets the value TEST_CH to the number of the wireless channel indicated by the wireless channel information. Thus, the number of the wireless channel indicated by the value TEST_CH is the same as the number of the wireless channel indicated by the wireless channel information.

After the value TEST_CH is set, the second control unit 210 sets the value D_AMOUNT[TEST_CH] to 0 (step S2203). After D_AMOUNT[TEST_CH] is set to 0, the second control unit 210 clears the channel-monitoring time timer (step S2204). Thereby, the time measured by the channel-monitoring time timer is initialized. After the channel-monitoring time timer is cleared, the process of step S220 ends.

In the above-described step S221, the second control unit 210 sets the wireless channel indicated by the value TEST_CH in the third wireless communication unit 201. The value TEST_CH is the number of the wireless channel indicated by a test channel change instruction packet. Thereby, the same wireless channel as the wireless channel set in the first wireless communication unit 106 of the endoscope 100 is set in the third wireless communication unit 201. The second control unit 210 sequentially changes the wireless channel at an interval of a previously designated time, i.e., a time corresponding to the channel test time in the endoscope 100, to receive the test data through the third wireless communication unit 201.

Figure 15:
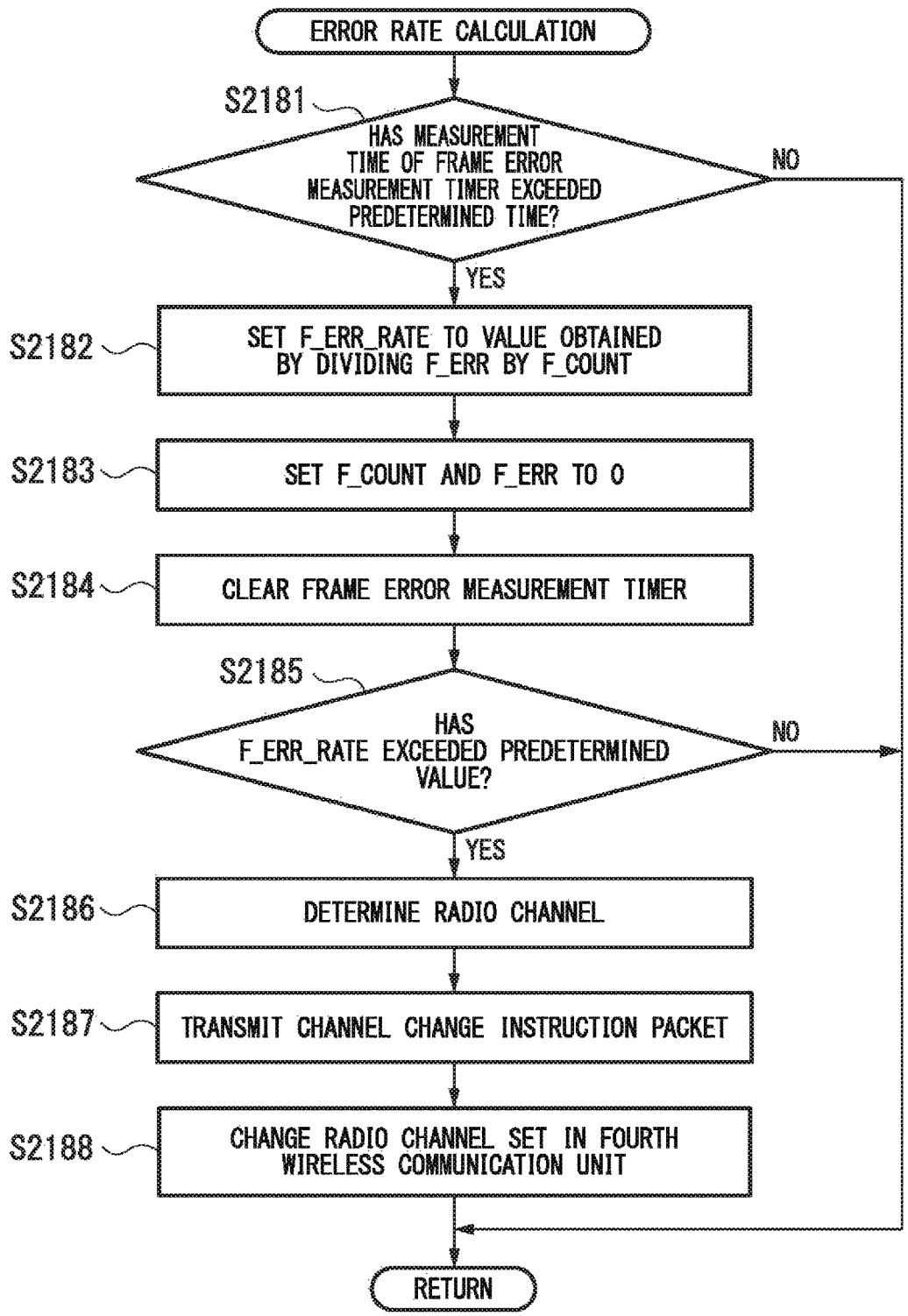
FIG. 15 is a flowchart illustrating a procedure example of an operation of the reception device according to an embodiment of the present invention.

FIG. 15 illustrates details of step S218. The second control unit 210 determines whether a time measured by the frame error measurement timer exceeds a predetermined time (step S2181). For example, the predetermined time is a time obtained by multiplying the time of one frame by a natural number. When the time measured by the frame error measurement timer does not exceed the predetermined time, the process of step S218 ends.

When the time measured by the frame error measurement timer exceeds the predetermined time, the second control unit 210 sets the value F_ERR_RATE to a value obtained by dividing the value F_ERR by the value F_COUNT (step S2182). The value F_ERR_RATE indicates an error rate of the moving-image data, i.e., communication quality of the wireless channel used in the transmission of the moving-image data. The value F_RRR_RATE is the same as a value obtained by dividing the value F_ERR by the value F_COUNT. The value F_ERR_RATE is stored in the second RAM 209.

After the value F_ERR_RATE is set, the second control unit 210 sets the value F_COUNT and the value F_ERR to 0 (step S2183). After the value F_COUNT and the value F_ERR are set to 0, the second control unit 210 clears the frame error measurement timer (step S2184). Thereby, the time measured by the frame error measurement timer is initialized.

After the frame error measurement timer is cleared, the second control unit 210 determines whether the value F_ERR_RATE exceeds a predetermined value (step S2185). That is, the second control unit 210 determines whether the error rate of the moving-image data exceeds the predetermined time. In other words, the second control unit 210 determines whether the communication quality of the wireless channels used by the second wireless communication unit 108 and the fourth wireless communication unit 203 is less than predetermined quality. When the value F_ERR_RATE does not exceed the predetermined value, i.e., when the communication quality of the wireless channels used by the second wireless communication unit 108 and the fourth wireless communication unit 203 is greater than or equal to the predetermined quality, the process of step S218 ends.

When the value F_ERR_RATE exceeds the predetermined value, i.e., when the communication quality of the wireless channels used by the second wireless communication unit 108 and the fourth wireless communication unit 203 is less than the predetermined quality, the second control unit 210 determines a wireless channel used in the transmission of moving-image data, i.e., a wireless channel set in the fourth wireless communication unit 203 (step S2186). At this time, the second control unit 210 determines the wireless channel on the basis of the value CH_STATUS[n]. The value CH_STATUS[n] indicates a communication rate of an $n^{th}$ wireless channel. The value CH_STATUS[n] is communication quality information about communication quality of a wireless channel on which test data is received. That is, in step S2186, the second control unit 210 determines the wireless channel on the basis of the communication quality information. For example, the second control unit 210 selects a wireless channel corresponding to a largest value CH_STATUS[n] among values CH_STATUS[n] corresponding to a plurality of wireless channels.

The second control unit 210 may determine the wireless channel so that the wireless channel set in the fourth wireless communication unit 203 is different from the wireless channel set in the third wireless communication unit 201. Alternatively, when the determined wireless channel is the same as the wireless channel set in the third wireless communication unit 201, the second control unit 210 may change the wireless channel set in the third wireless communication unit 201 to a wireless channel different from the determined wireless channel. When the wireless channel set in the third wireless communication unit 201 is changed, it is desirable that the second control unit 210 transmit the test channel change instruction packet to the endoscope 100 through the third wireless communication unit 201 or the fourth wireless communication unit 203.

After the wireless channel is determined, the second control unit 210 generates a channel change instruction packet and transmits the generated channel change instruction packet to the endoscope 100 through the third wireless communication unit 201 or the fourth wireless communication unit 203 (step S2187). The channel change instruction packet includes wireless channel information indicating the wireless channel determined in step S2186.

After the channel change instruction packet is transmitted, the second control unit 210 sets the wireless channel determined in step S2186 in the fourth wireless communication unit 203 (step S2188). That is, the second control unit 210 sets the wireless channel determined from communication quality information in the fourth wireless communication unit 203. Thereby, the wireless channel set in the fourth wireless communication unit 203 is changed. After the wireless channel is changed, the process of step S218 ends.

Details of the processes illustrated in FIGS. 10 to 15 can be appropriately changed.

As described above, in the first operation example, the second control unit 210 of the reception device 200 generates communication quality information about communication quality of a wireless channel used in the transmission of the test data (step S2201). When the communication quality of the wireless channel used by the fourth wireless communication unit 203 is less than predetermined quality, the second control unit 210 determines the wireless channel on the basis of the generated communication quality information (step S2186). The second control unit 210 sets the determined wireless channel in the fourth wireless communication unit 203 (step S2188).

The third wireless communication unit 201 or the fourth wireless communication unit 203 transmits the wireless channel information indicating the determined wireless channel to the endoscope 100 (step S2187). The first wireless communication unit 106 or the second wireless communication unit 108 of the endoscope 100 receives the wireless channel information from the reception device 200 (step S116). The first control unit 112 sets the wireless channel indicated by the received wireless channel information in the second wireless communication unit 108 (step S117).

When the communication quality of the wireless channels used by the second wireless communication unit 108 and the fourth wireless communication unit 203 is less than predetermined quality in the first operation example, the wireless channels to be used by the second wireless communication unit 108 and the fourth wireless communication unit 203 are changed. Communication of test data is performed immediately after the endoscope 100 and the reception device 200 are powered on and the wireless channels to be used by the second wireless communication unit 108 and the fourth wireless communication unit 203 may be determined on the basis of a communication result.

A wireless communication unit using a wireless channel having better communication quality between the third wireless communication unit 201 and the fourth wireless communication unit 203 may transmit the wireless channel information to the endoscope 100. Likewise, a wireless communication unit using a wireless channel having better communication quality between the first wireless communication unit 106 and the second wireless communication unit 108 may receive the wireless channel information from the reception device 200.

SECOND OPERATION EXAMPLE

In the second operation example, the wireless channel used in the transmission of moving-image data is determined by the endoscope 100. FIGS. 16 to 19 illustrate procedure examples of the operation of the endoscope 100 in the second operation example. Description of the previously described process will be omitted.

Figure 16:
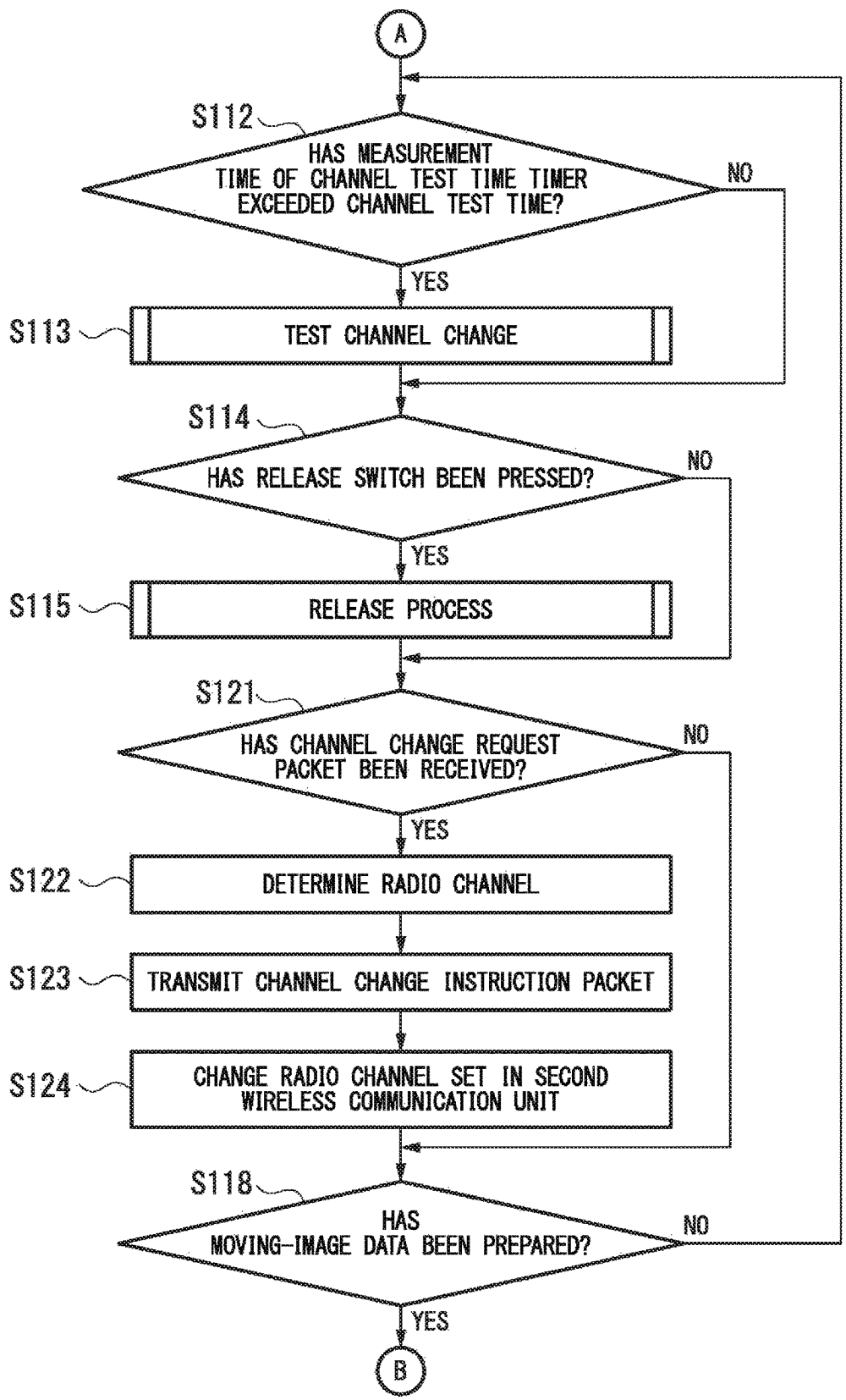
FIG. 16 is a flowchart illustrating a procedure example of an operation of the endoscope according to an embodiment of the present invention.

The endoscope 100 performs the processes illustrated in FIGS. 4 and 16 in place of the processes illustrated in FIGS. 4 and 5. For the process illustrated in FIG. 4, only parts different from the process in the first operation example will be described.

In step S101, the first control unit 112 performs the following process in addition to the process described in the first operation example. The first control unit 112 sets the value D_AMOUNT[n] indicating an amount of data received for each wireless channel and the value CH_STATUS[n] indicating a communication rate for each wireless channel to initial values. For example, the initial values are 0. The value D_AMOUNT[n] and the value CH_STATUS[n] are stored in the first RAM 111.

In the process illustrated in FIG. 16, step S116 in the process illustrated in FIG. 5 is changed to step S121. In the process illustrated in FIG. 16, steps S122 and S123 are added to the process illustrated in FIG. 5. In the process illustrated in FIG. 16, step S117 in the process illustrated in FIG. 5 is changed to step S124. For the process illustrated in FIG. 16, only parts different from the process illustrated in FIG. 5 will be described.

When the release switch is not pressed in step S114 or when the process of step S115 is performed, the first control unit 112 awaits the reception of a channel change request packet transmitted from the reception device 200 (step S121). The channel change request packet is a packet for requesting the change of the wireless channel. When the channel change request packet is transmitted from the reception device 200, the first control unit 112 receives the channel change request packet through the first wireless communication unit 106 or the second wireless communication unit 108.

When no channel change request packet is received, the process of step S118 is performed. When the channel change request packet is received, the first control unit 112 determines a wireless channel used in the transmission of the moving-image data, i.e., a wireless channel set in the second wireless communication unit 108 (step S122). At this time, the first control unit 112 determines the wireless channel on the basis of the value CH_STATUS[n]. The value CH_STATUS[n] indicates a communication rate of an $n^{th}$ wireless channel. The value CH_STATUS[n] is communication quality information about communication quality of a wireless channel on which test data is received. That is, the first control unit 112 determines the wireless channel on the basis of the communication quality information in step S122. For example, the first control unit 112 selects a wireless channel corresponding to a largest value CH_STATUS[n] among values CH_STATUS[n] corresponding to a plurality of wireless channels. The reception device 200 calculates the value CH_STATUS[n] in the first operation example, but the endoscope 100 calculates the value CH_STATUS[n] in the second operation example.

The first control unit 112 may determine the wireless channel so that the wireless channel set in the second wireless communication unit 108 is different from the wireless channel set in the first wireless communication unit 106. Alternatively, when the determined wireless channel is the same as the wireless channel set in the first wireless communication unit 106, the first control unit 112 may change the wireless channel set in the first wireless communication unit 106 to a wireless channel different from the determined wireless channel. When the wireless channel set in the first wireless communication unit 106 is changed, it is desirable that the first control unit 112 transmit the test channel change instruction packet to the reception device 200 through the first wireless communication unit 106 or the second wireless communication unit 108.

After the wireless channel is determined, the first control unit 112 generates a channel change instruction packet and transmits the generated channel change instruction packet to the reception device 200 through the first wireless communication unit 106 or the second wireless communication unit 108 (step S123). As described above, the channel instruction packet is a packet for issuing a change of the wireless channel used in the transmission of the moving-image data.

The channel change instruction packet includes wireless channel information indicating the wireless channel determined in step S122.

After the channel change instruction packet is transmitted, the first control unit 112 sets the wireless channel determined in step S122 in the second wireless communication unit 108 (step S124). That is, the first control unit 112 sets the wireless channel determined from communication quality information about communication quality of the wireless channel used in the transmission of the test data in the second wireless communication unit 108. Thereby, the wireless channel set in the second wireless communication unit 108 is changed.

Figure 17:
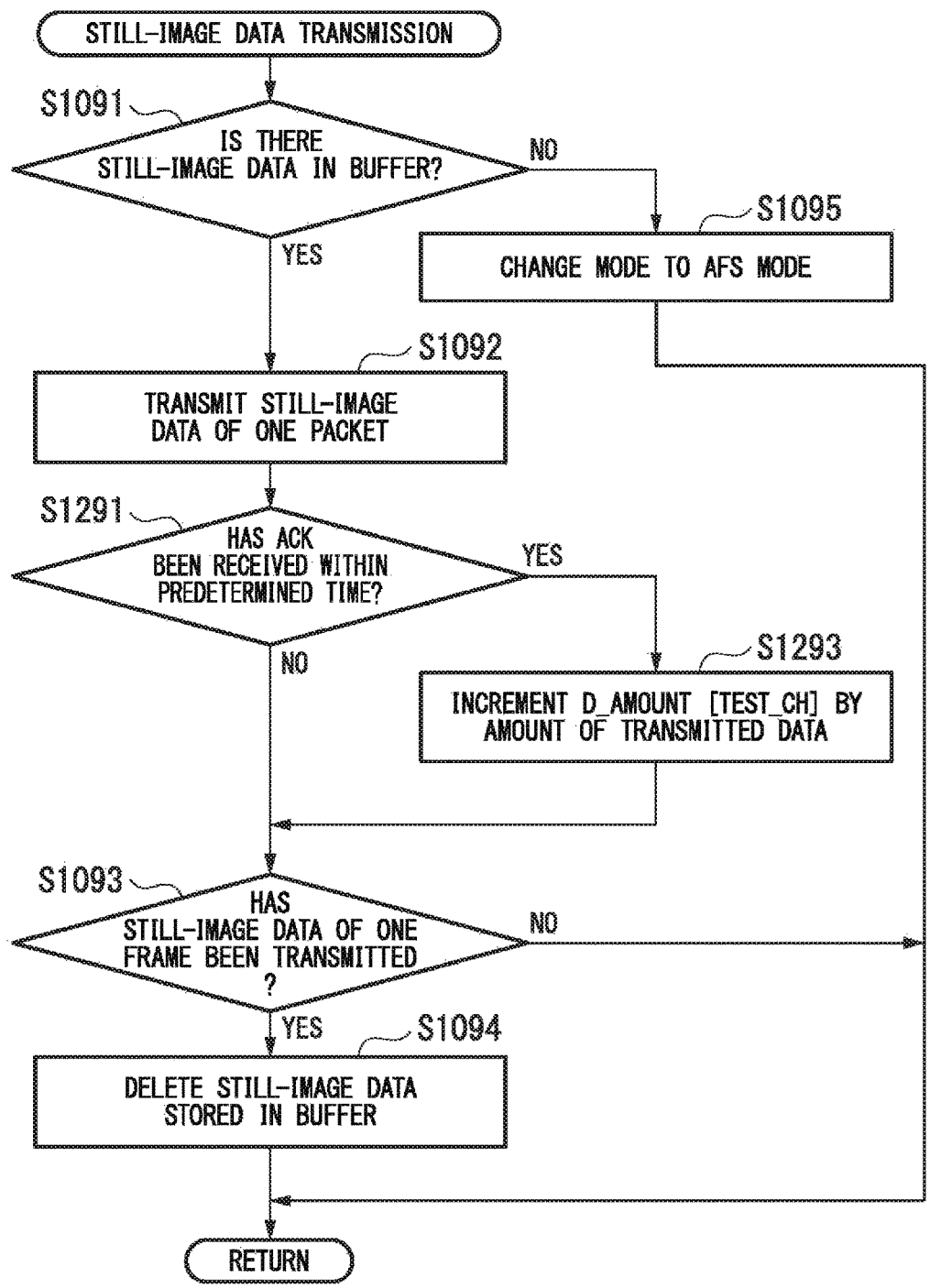
FIG. 17 is a flowchart illustrating a procedure example of an operation of the endoscope according to an embodiment of the present invention.

FIG. 17 illustrates details of step S109 of the process illustrated in FIG. 4. In the process illustrated in FIG. 17, steps S1291 and S1292 are added to the process illustrated in FIG. 7. For the process illustrated in FIG. 17, only parts different from the process illustrated in FIG. 7 will be described.

After the still-image data is transmitted in step S1092, the first control unit 112 awaits the reception of an ACK transmitted from the reception device 200 for a predetermined time from a point in time at which the still-image data is transmitted (step S1291). The ACK is a packet to be transmitted from the reception device 200 when data transmitted from the endoscope 100 is received normally. The ACK is reception information indicating that the still-image data is received. When the ACK is transmitted from the reception device 200, the first control unit 112 receives the ACK through the first wireless communication unit 106. The first control unit 112 may receive information corresponding to the ACK through the second wireless communication unit 108.

When no ACK is received within the predetermined time from the point in time at which the still-image data is transmitted, the process of step S1093 is performed. When the ACK is received within the predetermined time from the point in time at which the still-image data is transmitted, the first control unit 112 increments the value D_AMOUNT [TEST_CH] by an amount of transmitted data (step S1292). The amount of transmitted data may be the number of transmitted packets. After the value D_AMOUNT[TEST_CH] is updated, the process of step S1093 is performed.

Figure 18:
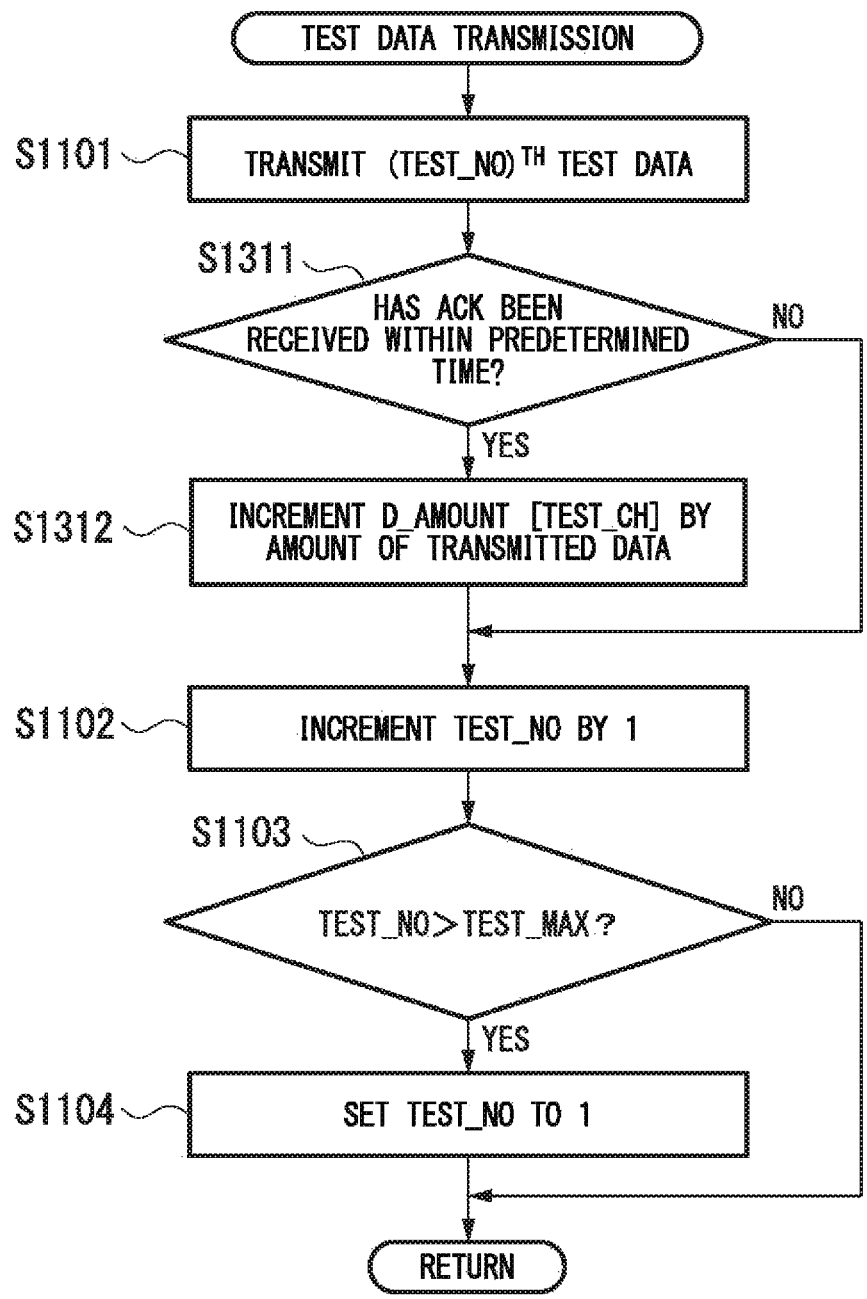
FIG. 18 is a flowchart illustrating a procedure example of an operation of the endoscope according to an embodiment of the present invention.

FIG. 18 illustrates details of the process of step S110 illustrated in FIG. 4. In the process illustrated in FIG. 18, steps S1311 and S1312 are added to the process illustrated in FIG. 8. For the process illustrated in FIG. 18, only parts different from the process illustrated in FIG. 8 will be described.

After the test data is transmitted in step S1101, the first control unit 112 awaits the reception of an ACK transmitted from the reception device 200 for a predetermined time from a point in time at which the test data is transmitted (step S1311). The ACK received in step S1311 is reception information indicating that the test data is received. When the ACK is transmitted from the reception device 200, the first control unit 112 receives the ACK through the first wireless communication unit 106. The first control unit 112 may receive information corresponding to the ACK through the second wireless communication unit 108.

When no ACK is received within the predetermined time from the point in time at which the test data is transmitted, the process of step S1102 is performed. When the ACK is received within the predetermined time from the point in time at which the test data is transmitted, the first control unit 112 increments the value D_AMOUNT[TEST_CH] by an amount of transmitted data (step S1312). The amount of transmitted data may be the number of transmitted packets. Next, the process of step S1102 is performed.

Figure 19:
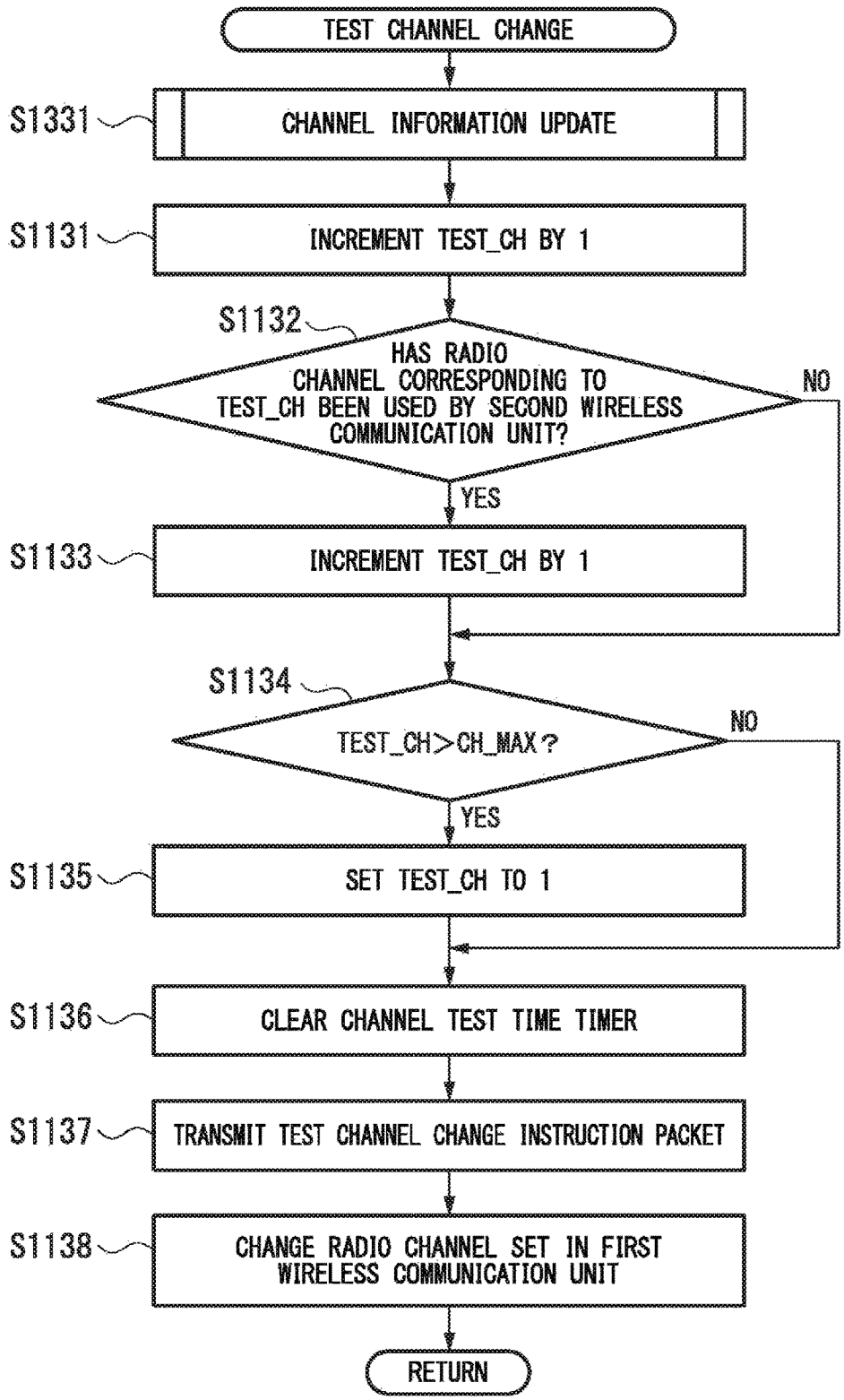
FIG. 19 is a flowchart illustrating a procedure example of an operation of the endoscope according to an embodiment of the present invention.

FIG. 19 illustrates details of the process of step S113 illustrated in FIG. 16. In the process illustrated in FIG. 19, step S1331 is added to the process illustrated in FIG. 9. For the process illustrated in FIG. 19, only parts different from the process illustrated in FIG. 9 will be described.

Figure 20:
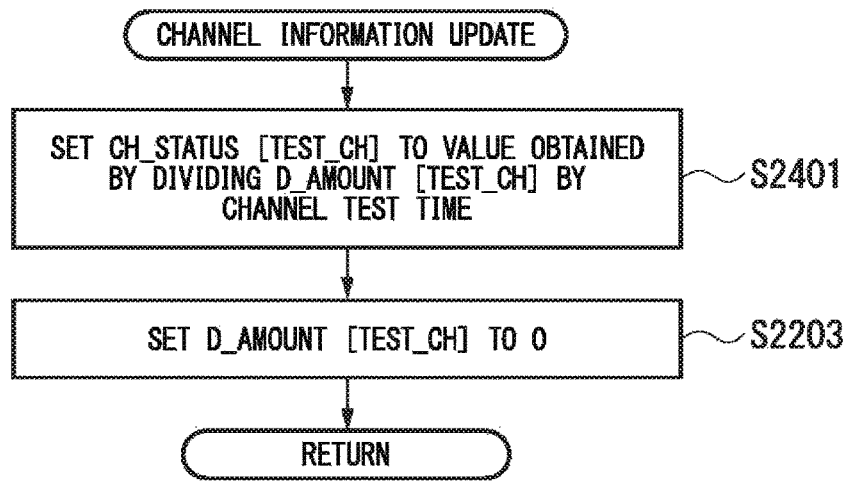
FIG. 20 is a flowchart illustrating a procedure example of an operation of the endoscope according to an embodiment of the present invention.

Before the process of step S1131 is performed, information about the wireless channel is updated (step S1331). FIG. 20 illustrates details of step S1331 of the process illustrated in FIG. 19. In the process illustrated in FIG. 20, steps S2202 and S2204 are removed from the process illustrated in FIG. 14. In the process illustrated in FIG. 20, step S2201 of the process illustrated in FIG. 14 is changed to step S2401. For the process illustrated in FIG. 20, only parts different from the process illustrated in FIG. 14 will be described.

In step S2401, the first control unit 112 sets the value CH_STATUS[TEST_CH] to a value obtained by dividing the value D_AMOUNT[TEST CH] by a time for which the value D_AMOUNT[TEST_CH] is measured by a channel test time timer. The value D_AMOUNT[TEST_CH] is updated when the ACK transmitted from the reception device 200, i.e., reception information, is received. The value CH_STATUS[n] is communication quality information about communication quality of a wireless channel on which test data is received. Therefore, in step S2401, the first control unit 112 generates the communication quality information on the basis of the reception information. Thus, in step S122 of FIG. 16, the wireless channel is determined on the basis of the value CH_STATUS[TEST_CH].

After the value CH_STATUS[TEST_CH] is set, D_AMOUNT[TEST_CH] is set to 0 in step S2203. After D_AMOUNT[TEST_CH] is set to 0, the process of step S1331 ends.

FIGS. 21 to 25 illustrate procedure examples of an operation of the reception device 200 in the second operation example. Description of the previously described process will be omitted.

Figure 21:
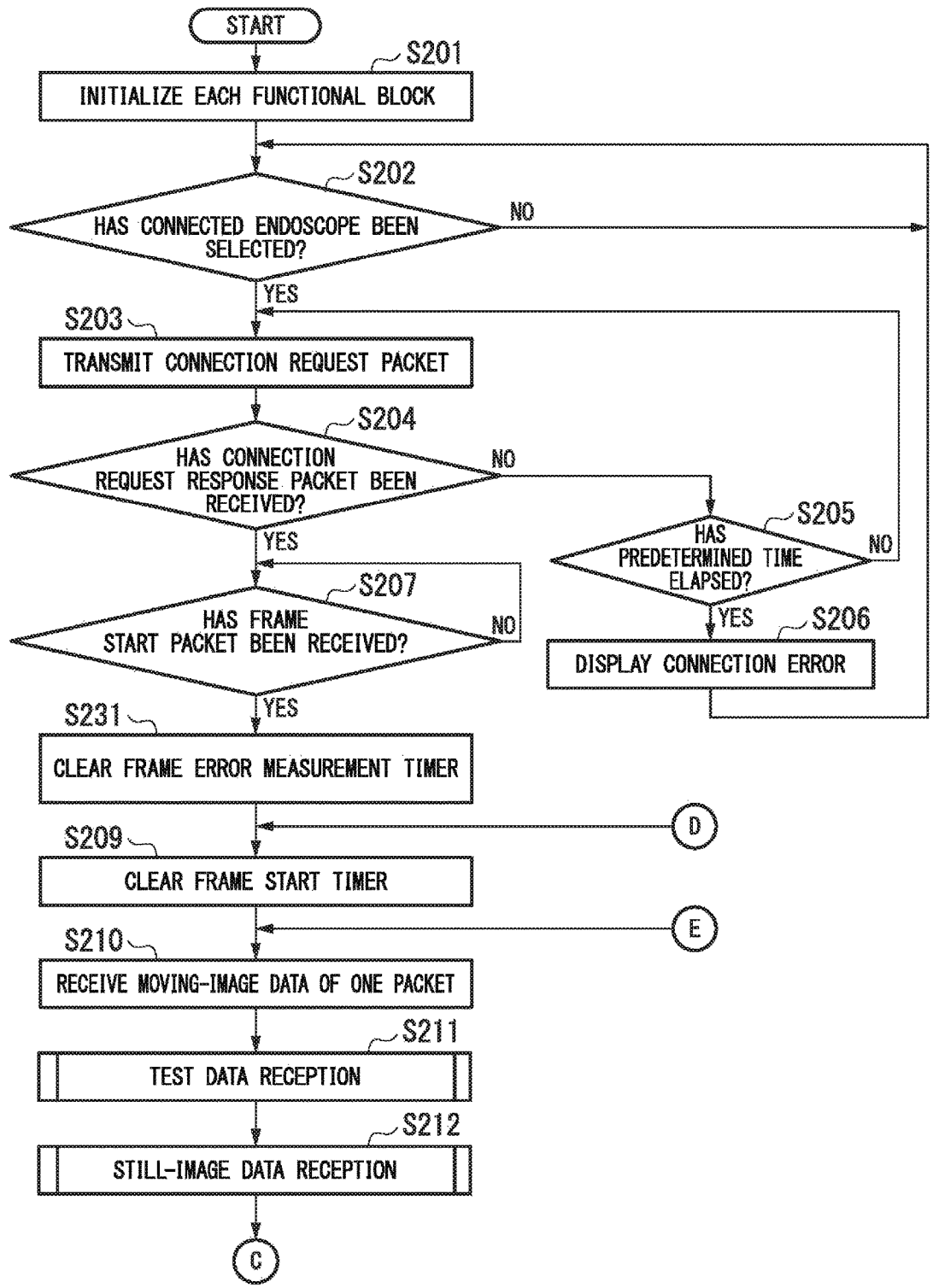
FIG. 21 is a flowchart illustrating a procedure example of an operation of the reception device according to an embodiment of the present invention.
Figure 22:
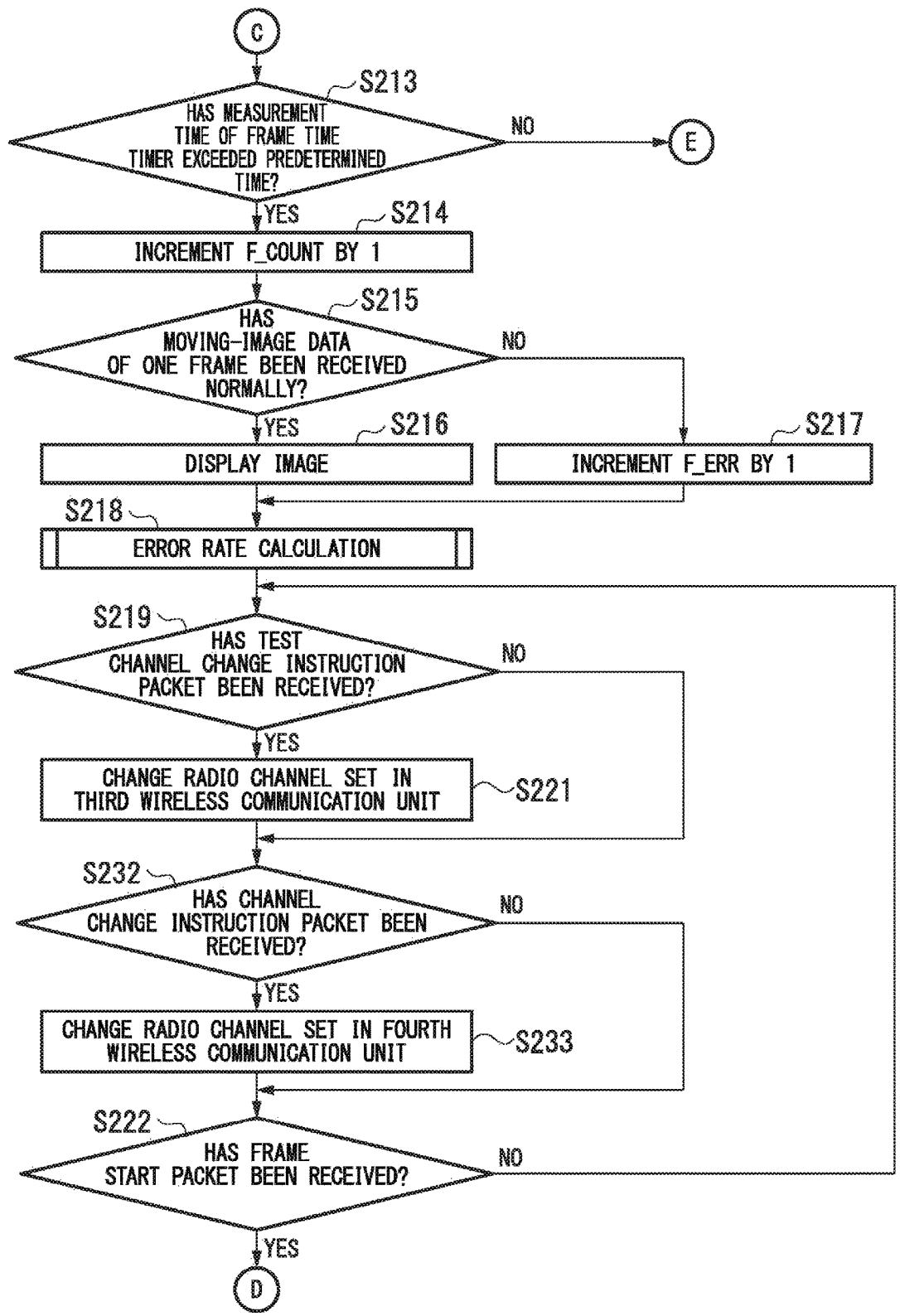
FIG. 22 is a flowchart illustrating a procedure example of an operation of the reception device according to an embodiment of the present invention.

The reception device 200 performs processes illustrated in FIGS. 21 and 22 in place of the processes illustrated in FIGS. 10 and 11. In FIG. 21, step S231 is added to FIG. 10. For the process illustrated in FIG. 21, only parts different from the process illustrated in FIG. 10 will be described.

When a frame start packet is received in step S207, the second control unit 210 clears a frame error measurement timer (step S231). Thereby, the time measured by the frame error measurement timer is initialized. As described above, the frame error measurement timer is a timer for measuring a time for which the number of occurrences of an error of the moving-image data is detected. After the frame error measurement timer is cleared, the process of step S209 is performed.

In FIG. 22, step S220 is removed from FIG. 11. In the process illustrated in FIG. 22, steps S232 and S233 are added to the process illustrated in FIG. 11. For the process illustrated in FIG. 22, only parts different from the process illustrated in FIG. 11 will be described.

When no test channel change instruction packet is received in step S219 or when the wireless channel set in the third wireless communication unit 201 is changed in step S221, the second control unit 210 awaits the reception of the channel change instruction packet transmitted from the endoscope 100 (step S232). When the channel change instruction packet is transmitted from the reception device 200, the first control unit 112 receives the channel change instruction packet through the first wireless communication unit 106 or the second wireless communication unit 108.

When the channel change instruction packet is received, the second control unit 210 sets a wireless channel indicated by wireless channel information included in the channel change instruction packet in the fourth wireless communication unit 203 (step S233). That is, the second control unit 210 sets the wireless channel determined from communication quality information about the communication quality of the wireless channel used in the transmission of the test data in the fourth wireless communication unit 203. Thereby, the wireless channel set in the fourth wireless communication unit 203 is changed. After the wireless channel is changed, the process of step S222 is performed.

Figure 23:
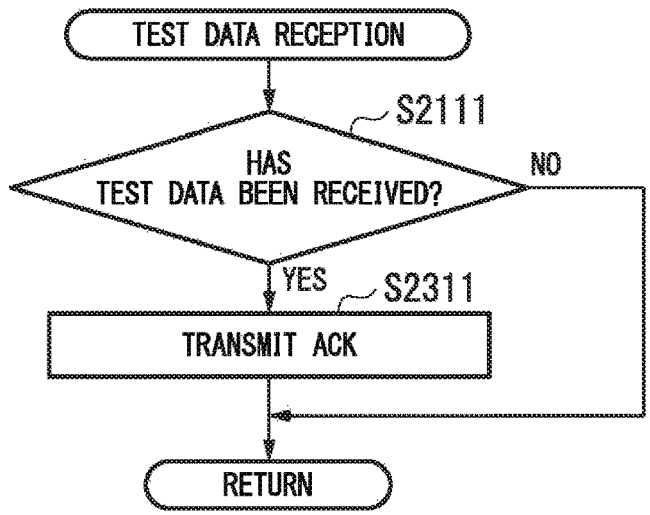
FIG. 23 is a flowchart illustrating a procedure example of an operation of the reception device according to an embodiment of the present invention.

FIG. 23 illustrates details of step S211 of the process illustrated in FIG. 21. In the process illustrated in FIG. 23, step S2112 is removed from the process illustrated in FIG. 12. In the process illustrated in FIG. 23, step S2311 is added to the process illustrated in FIG. 12. For the process illustrated in FIG. 23, only parts different from the process illustrated in FIG. 12 will be described.

When the test data is received in step S2111, the second control unit 210 generates an ACK and transmits the generated ACK to the endoscope 100 through the third wireless communication unit 201 (step S2311). The second control unit 210 may transmit information corresponding to the ACK to the endoscope 100 through the fourth wireless communication unit 203. After the ACK is transmitted, the process of step S211 ends.

Figure 24:
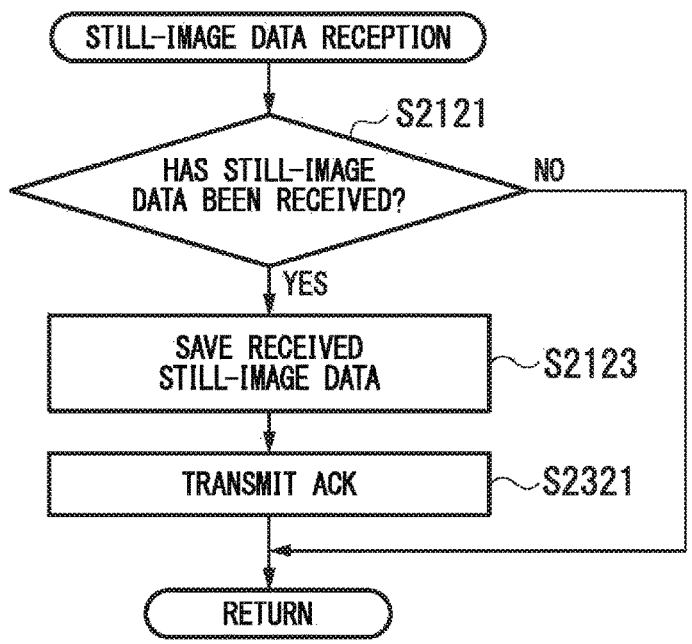
FIG. 24 is a flowchart illustrating a procedure example of an operation of the reception device according to an embodiment of the present invention.

FIG. 24 illustrates details of step S212 of the process illustrated in FIG. 21. In the process illustrated in FIG. 24, step S2122 is removed from the process illustrated in FIG. 13. In the process illustrated in FIG. 24, step S2331 is added to the process illustrated in FIG. 13. For the process illustrated in FIG. 24, only parts different from the process illustrated in FIG. 13 will be described.

When the still-image data is received in step S2121, the second control unit 210 saves the received still-image data in the image data storage unit 207 (step S2123). After the still-image data is saved, the second control unit 210 generates an ACK and transmits the generated ACK to the endoscope 100 through the third wireless communication unit 201 (step S2321). The second control unit 210 may transmit information corresponding to the ACK to the endoscope 100 through the fourth wireless communication unit 203. After the ACK is transmitted, the process of step S212 ends.

Figure 25:
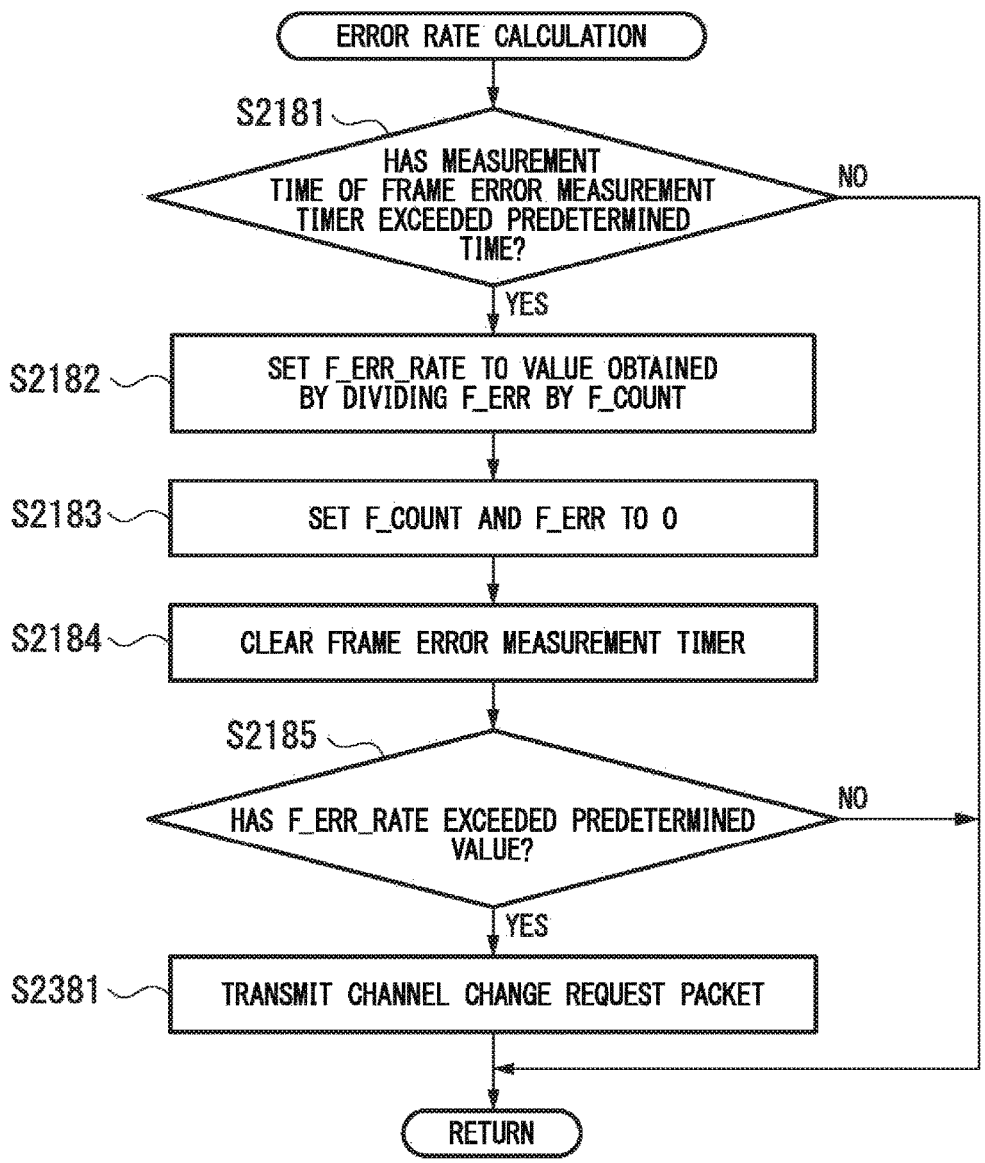
FIG. 25 is a flowchart illustrating a procedure example of an operation of the reception device according to an embodiment of the present invention.

FIG. 25 illustrates details of step S218 of the process illustrated in FIG. 22. In the process illustrated in FIG. 25, steps S2186 and S2188 are removed from the process illustrated in FIG. 15. In the process illustrated in FIG. 25, step S2187 of the process illustrated in FIG. 15 is changed to step S2381. For the process illustrated in FIG. 25, only parts different from the process illustrated in FIG. 15 will be described.

When a value F_ERR_RATE exceeds a predetermined value in step S2185, the second control unit 210 generates a channel change request packet and transmits the generated channel change request packet to the endoscope 100 through the third wireless communication unit 201 or the fourth wireless communication unit 203 (step S2381). After the channel change request packet is transmitted, the process of step S2180 ends.

As described above, in the second operation example, the third wireless communication unit 201 or the fourth wireless communication unit 203 of the reception device 200 transmits reception information indicating that test data is received to the endoscope 100 (step S2311). The first wireless communication unit 106 or the second wireless communication unit 108 of the endoscope 100 receives the reception information from the reception device 200 (step S1311). The first control unit 112 generates communication quality information about communication quality of a wireless channel used in the transmission of the test data on the basis of the received reception information (step S2201). The first control unit 112 determines a wireless channel on the basis of the generated communication quality information (step S122).

The first control unit 112 sets the determined wireless channel in the second wireless communication unit 108 (step S124). The first wireless communication unit 106 or the second wireless communication unit 108 transmits the wireless channel information indicating the determined wireless channel to the reception device 200 (step S123). The third wireless communication unit 201 or the fourth wireless communication unit 203 of the reception device 200 receives the wireless channel information from the endoscope 100 (step S232). The second control unit 210 sets the wireless channel indicated by the received wireless channel information in the fourth wireless communication unit 203 (step S233).

The wireless communication unit using a wireless channel having better communication quality between the first wireless communication unit 106 and the second wireless communication unit 108 may receive the reception information from the reception device 200. Likewise, the wireless communication unit using a wireless channel having better communication quality between the third wireless communication unit 201 and the fourth wireless communication unit 203 may transmit the reception information to the endoscope 100.

THIRD OPERATION EXAMPLE

The third operation example is a modified example of the second operation example. In the third operation example, still-image data is transmitted using a fixed wireless channel. In the third operation example, the process illustrated in FIG. 6 is changed to a process illustrated in FIG. 26. The process illustrated in FIG. 19 is changed to a process illustrated in FIG. 27. A process other than the processes illustrated in FIGS. 26 and 27 is similar to the process in the second operation example.

Figure 26:
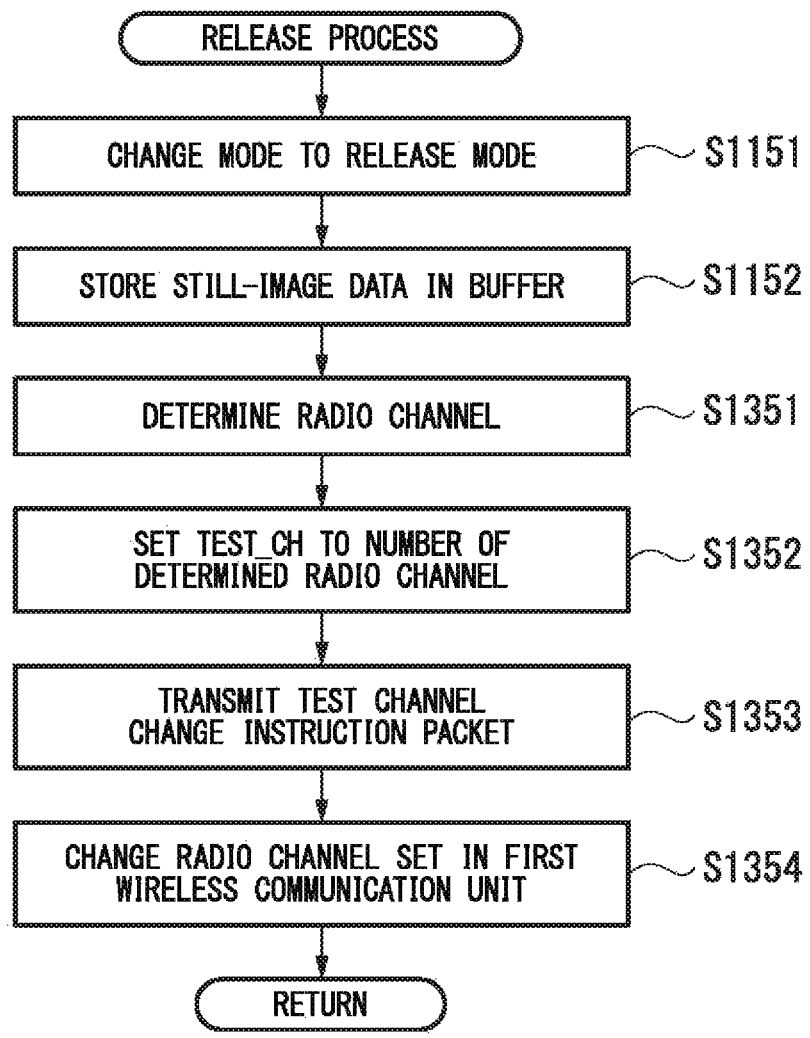
FIG. 26 is a flowchart illustrating a procedure example of an operation of the endoscope according to an embodiment of the present invention.
Figure 27:
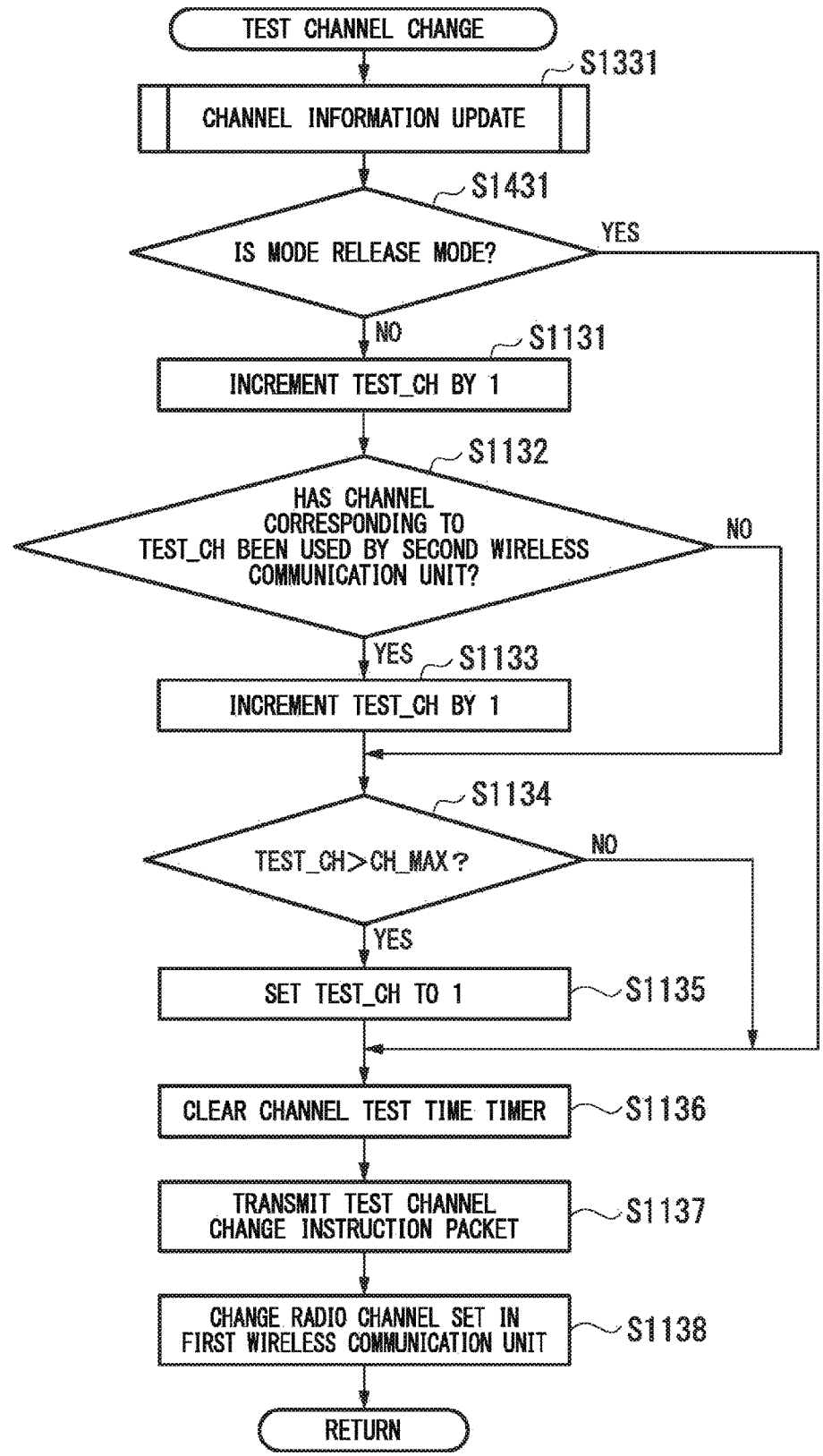
FIG. 27 is a flowchart illustrating a procedure example of an operation of the endoscope according to an embodiment of the present invention.

In FIG. 26, steps S1351, S1352, S1353, and S1354 are added to the process illustrated in FIG. 6. For the process illustrated in FIG. 26, only parts different from the process illustrated in FIG. 6 will be described.

After still-image data is stored in the buffer in step S1152, the first control unit 112 determines a wireless channel used in the transmission of the still-image data, i.e., a wireless channel set in the first wireless communication unit 106 (step S1351). At this time, the first control unit 112 determines the wireless channel on the basis of the value CH_STATUS[n]. The value CH_STATUS[n] indicates a communication rate of an $n^{th}$ wireless channel. The value CH_STATUS[n] is communication quality information about communication quality of a wireless channel on which test data is received. That is, the first control unit 112 determines the wireless channel on the basis of the communication quality information in step S1351. For example, the first control unit 112 selects a wireless channel corresponding to a largest value CH_STATUS[n] among values CH_STATUS[n] corresponding to a plurality of wireless channels.

After the wireless channel is determined, the first control unit 112 sets the value TEST_CH to the number of the determined wireless channel (step S1352). Thereby, the value TEST_CH is updated by the number of the determined wireless channel.

After the value TEST_CH is set, the first control unit 112 generates a test channel change instruction packet and transmits the generated test channel change instruction packet to the reception device 200 through the first wireless communication unit 106 or the second wireless communication unit 108 (step S1353). The test channel change instruction packet transmitted in step S1353 is a packet for issuing an instruction for setting a wireless channel to be used in the transmission of the still-image data. The test channel change instruction packet includes wireless channel information indicating the wireless channel to be used in the transmission of the still-image data. A value indicated by the wireless channel information is the same as the value TEST_CH. When the test channel change instruction packet is received by the reception device 200, the wireless channel set in the third wireless communication unit 201 is changed in the process of step S221.

After the test channel change instruction packet is transmitted, the first control unit 112 sets a wireless channel indicated by the value TEST_CH in the first wireless communication unit 106 (step S1354). Thereby, the wireless channel set in the first wireless communication unit 106 is changed. After the wireless channel is changed, the process of step S115 ends.

In the process illustrated in FIG. 27, step S1431 are added to the process illustrated in FIG. 19. For the process illustrated in FIG. 27, only parts different from the process illustrated in FIG. 19 will be described.

After information about the wireless channel is updated in step S1331, the first control unit 112 determines whether the mode of the endoscope 100 is the release mode on the basis of information indicating the mode of the endoscope 100 (step S1431). Information indicating the mode of the endoscope 100 is stored in the first RAM 111.

When the mode of the endoscope 100 is the release mode, the process of step S1136 is performed. When the mode of the endoscope 100 is not the release mode, i.e., when the mode of the endoscope 100 is the AFS mode, the process of step S1131 is performed.

When the mode of the endoscope 100 is the release mode, the value TEST_CH is not changed and therefore the wireless channel to be set in the first wireless communication unit 106 in step S1138 is the same as the wireless channel immediately previously set in the first wireless communication unit 106. That is, the wireless channel set in the first wireless communication unit 106 is not changed. Thus, the first wireless communication unit 106 transmits still-image data to the reception device 200 using only one wireless channel when the release switch receives an image-recording instruction from the user.

Because the value TEST_CH is not changed, the wireless channel indicated by the wireless channel information included in the test channel change instruction packet to be transmitted in step S1137 is not changed. Thus, the wireless channel set in the third wireless communication unit 201 of the reception device 200 is not changed. Therefore, the third wireless communication unit 201 receives still-image data from the endoscope 100 using only one wireless channel.

When the mode of the endoscope 100 is the release mode, it is unnecessary to perform the process of step S1137 and the process of step S1138.

FOURTH OPERATION EXAMPLE

Figure 29:
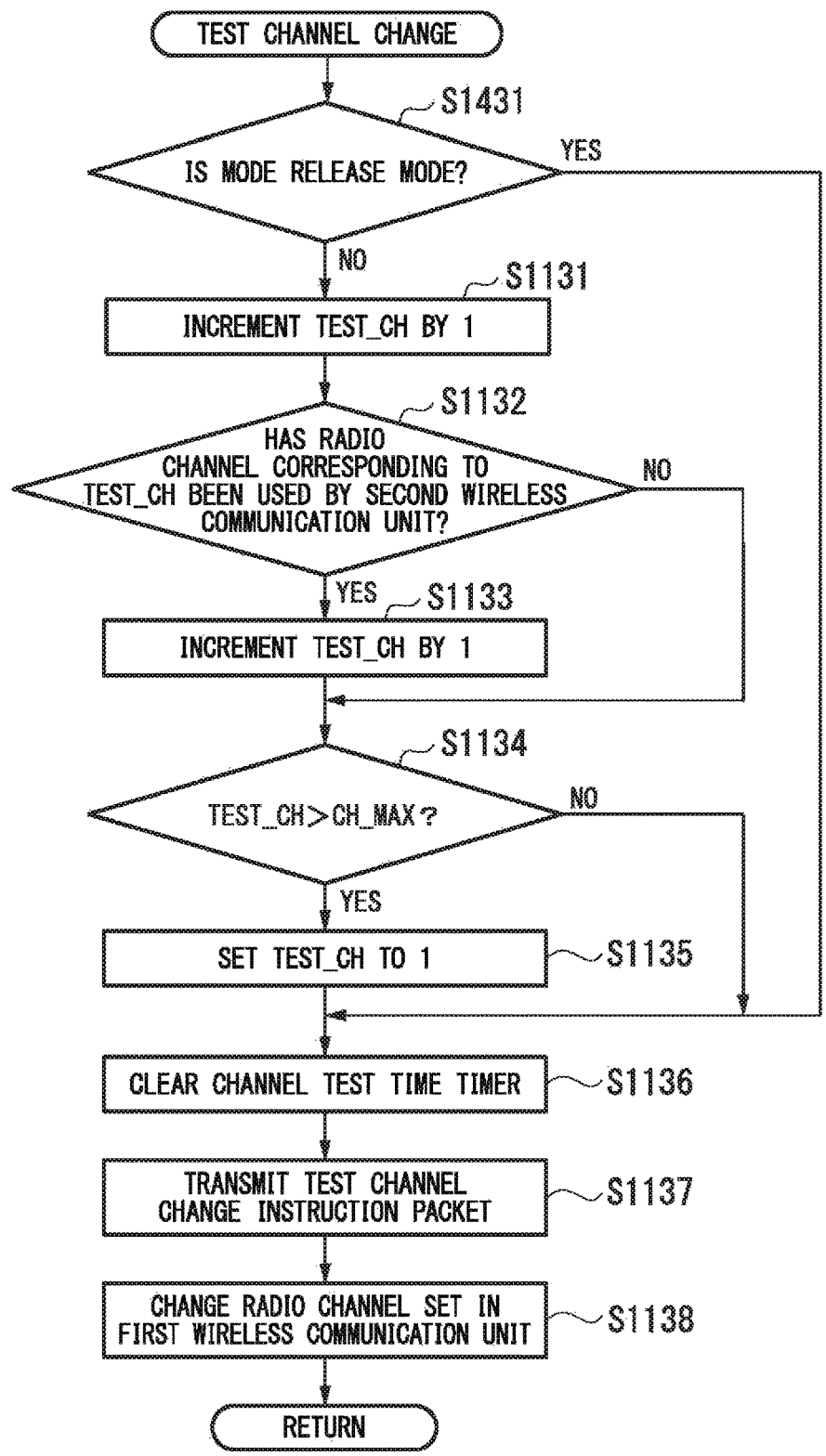
FIG. 29 is a flowchart illustrating a procedure example of an operation of the endoscope according to an embodiment of the present invention.
Figure 30:
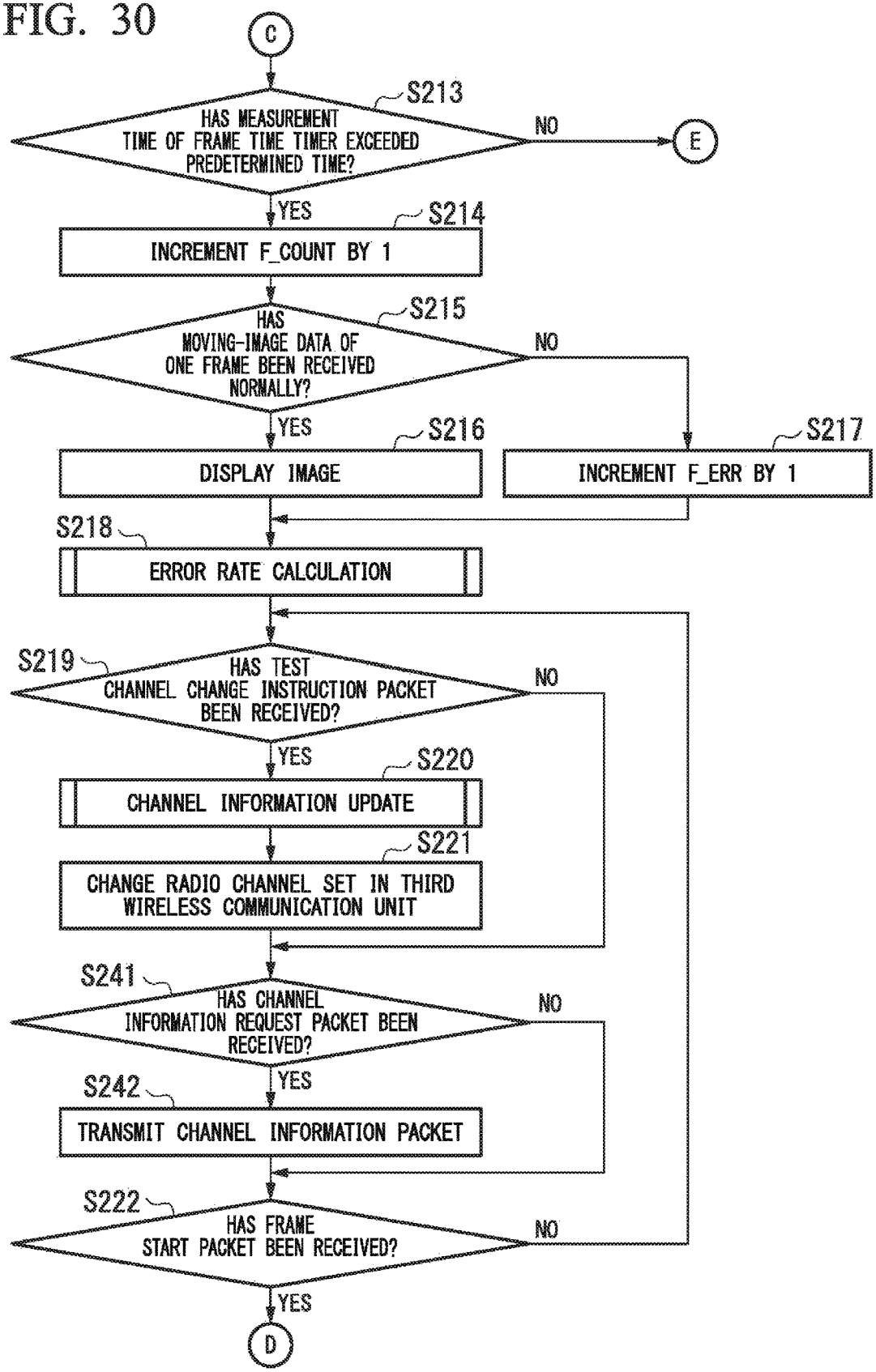
FIG. 30 is a flowchart illustrating a procedure example of an operation of the reception device according to an embodiment of the present invention.

The fourth operation example is a modified example of the first operation example. In the fourth operation example, still-image data is transmitted using a fixed wireless channel. In the fourth operation example, the process illustrated in FIG. 6 is changed to a process illustrated in FIG. 28. The process illustrated in FIG. 9 is changed to a process illustrated in FIG. 29. The process illustrated in FIG. 11 is changed to a process illustrated in FIG. 30. A process other than the processes illustrated in FIGS. 28, 29, 30 is similar to the process in the first operation example.

Figure 28:
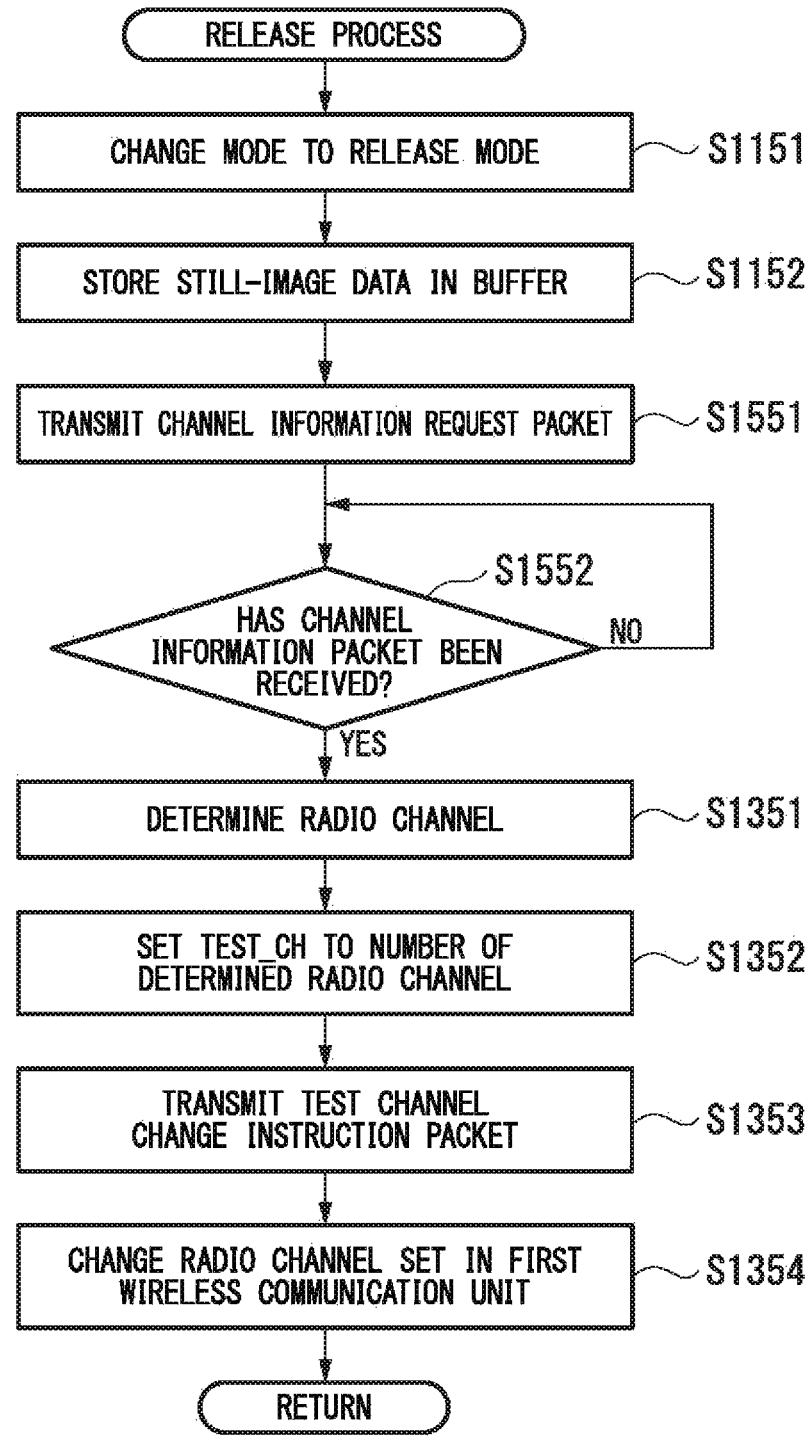
FIG. 28 is a flowchart illustrating a procedure example of an operation of the endoscope according to an embodiment of the present invention.

In the process illustrated in FIG. 28, steps S1551, S1552, and S1351 to S1354 are added to the process illustrated in FIG. 6. For the process illustrated in FIG. 28, only parts different from the process illustrated in FIG. 6 will be described.

After still-image data is stored in the buffer in step S1152, the first control unit 112 generates a channel information request packet and transmits the generated channel information request packet to the reception device 200 through the first wireless communication unit 106 or the second wireless communication unit 108 (step S1551). The channel information request packet is a packet for requesting information for determining the wireless channel to be used in the transmission of still-image data.

After the channel information request packet is transmitted, the first control unit 112 awaits the reception of the channel information packet to be transmitted from the reception device 200 (step S155). The channel information packet is a packet including the information for determining the wireless channel to be used in the transmission of the still-image data. Values CH_STATUS[n] for all wireless channels are included in the channel information packet. As described above, the value CH_STATUS[n] indicates a communication rate of an $n^{th}$ wireless channel. The value CH_STATUS[n] is communication quality information about communication quality of a wireless channel on which test data is received. When the channel information packet is transmitted from the reception device 200, the first control unit 112 receives the channel information packet through the first wireless communication unit 106 or the second wireless communication unit 108.

After the channel information packet is received, the process of step S1351 is performed. Steps S1351 to S1354 are similar to steps S1351 to S1354 illustrated in FIG. 26.

In FIG. 29, step S1431 is added to the process illustrated in FIG. 9. For the process illustrated in FIG. 29, only parts different from the process illustrated in FIG. 9 will be described.

The first control unit 112 determines whether the mode of the endoscope 100 is the release mode on the basis of information indicating the mode of the endoscope 100 (step S1431). The information indicating the mode of the endoscope 100 is stored in the first RAM 111.

When the mode of the endoscope 100 is the release mode, the process of step S1136 is performed. When the mode of the endoscope 100 is not the release mode, that is, when the mode of the endoscope 100 is the AFS mode, the process of step S1131 is performed.

As in the third operation example, the first wireless communication unit 106 transmits still-image data to the reception device 200 using only one wireless channel when the release switch receives an image-recording instruction from the user. The third wireless communication unit 201 receives still-image data from the endoscope 100 using only one wireless channel.

When the mode of the endoscope 100 is the release mode, it is unnecessary to perform the process of step S1137 and the process of S1138.

In FIG. 30, steps S241 and S242 are added to the process illustrated in FIG. 11. For the process illustrated in FIG. 30, only parts different from the process illustrated in FIG. 11 will be described.

When no test channel change instruction packet is received in step S219 or when the process of step S221 is performed, the second control unit 210 awaits the reception of a channel information request packet transmitted from the endoscope 100 (step S241). When the channel information request packet is transmitted from the endoscope 100, the second control unit 210 receives the channel information request packet through the third wireless communication unit 201 or the fourth wireless communication unit 203.

After the channel information request packet is received, the second control unit 210 generates a channel information packet and transmits the generated channel information packet to the endoscope 100 through the third wireless communication unit 201 or the fourth wireless communication unit 203 (step S242). As described above, the channel information packet includes values CH_STATUS[n] for all wireless channels. When no channel information request packet is received, no channel information packet is transmitted. After the channel information packet is transmitted, the process of step S222 is performed.

According to the present embodiment, the endoscope 100 includes: the imaging unit 101 configured to image a subject and output image data; the moving-image generation unit 102 configured to generate moving-image data from the image data output from the imaging unit 101; the still-image generation unit 103 configured to generate still-image data from the image data output from the imaging unit 101; a release instruction unit (the first operation unit 105) configured to receive an image-recording instruction from a user; the first wireless communication unit 106 configured to sequentially change a wireless channel to transmit test data used for detecting communication quality of each of a plurality of wireless channels to the reception device 200 and transmit the still-image data to the reception device 200 when the release instruction unit receives the image-recording instruction; the second wireless communication unit 108 configured to transmit the moving-image data to the reception device 200 using a wireless channel different from the wireless channel currently used by the first wireless communication unit 106; and a first setting unit (the first control unit 112) configured to set a wireless channel determined from communication quality information about the communication quality of the wireless channel used in the transmission of the test data in the second wireless communication unit 108.

According to the present embodiment, the reception device 200 includes: the third wireless communication unit 201 configured to sequentially change a wireless channel to receive test data used for detecting communication quality of each of a plurality of wireless channels from the endoscope 100 and receive still-image data from the endoscope 100; the fourth wireless communication unit 203 configured to receive moving-image data from the endoscope 100 using a wireless channel different from the wireless channel used by the third wireless communication unit 201; and a second setting unit (the second control unit 210) configured to set a wireless channel determined from communication quality information about the communication quality of the wireless channel used in the transmission of the test data in the fourth wireless communication unit 203.

According to the present embodiment, the wireless endoscope system 10 is configured to include the endoscope 100 and the reception device 200, wherein the endoscope 100 includes: the imaging unit 101 configured to image a subject and output image data; the moving-image generation unit 102 configured to generate moving-image data from the image data output from the imaging unit 101; the still-image generation unit 103 configured to generate still-image data from the image data output from the imaging unit 101; a release instruction unit (the first operation unit 105) configured to receive an image-recording instruction from a user; the first wireless communication unit 106 configured to sequentially change a wireless channel to transmit test data used for detecting communication quality of each of a plurality of wireless channels to the reception device 200 and transmit the still-image data to the reception device 200 when the release instruction unit receives the image-recording instruction; the second wireless communication unit 108 configured to transmit the moving-image data to the reception device 200 using a wireless channel different from the wireless channel currently used by the first wireless communication unit 106; and the first setting unit (the first control unit 112) configured to set a wireless channel determined from communication quality information about the communication quality of the wireless channel used in the transmission of the test data in the second wireless communication unit 108, and wherein the reception device 200 includes: the third wireless communication unit 201 configured to sequentially change a wireless channel to receive test data and receive still-image data; the fourth wireless communication unit 203 configured to receive moving-image data using a wireless channel different from the wireless channel used by the third wireless communication unit 201; and the second setting unit (the second control unit 210) configured to set a wireless channel determined from communication quality information in the fourth wireless communication unit 203.

According to the present embodiment, an image transmission method includes: the step S1101 of sequentially changing, by the first wireless communication unit 106, a wireless channel to transmit test data used for detecting communication quality of each of a plurality of wireless channels to the reception device 200; the step S1092 of transmitting, by the first wireless communication unit 106, still-image data generated from image data output from the imaging unit 101 to the reception device 200 when an image-recording instruction is received from a user; the step S107 of transmitting, by the second wireless communication unit 108, moving-image data generated from the image data to the reception device using a wireless channel different from the wireless channel currently used by the first wireless communication unit 106; and the step S117 of setting, by the first setting unit (the first control unit 112), a wireless channel determined from communication quality information about the communication quality of the wireless channel used in the transmission of the test data in the second wireless communication unit 108.

According to the present embodiment, an image reception method includes: the step S2111 of sequentially changing, by the third wireless communication unit 201, a wireless channel to receive test data used for detecting communication quality of each of a plurality of wireless channels from the endoscope 100; the step S2121 of receiving, by the third wireless communication unit 201, still-image data from the endoscope 100; the step S210 of receiving, by the fourth wireless communication unit 203, moving-image data from the endoscope 100 using a wireless channel different from the wireless channel used by the third wireless communication unit 201; and the step S2188 of setting, by the second setting unit (the second control unit 210), a wireless channel determined from communication quality information about the communication quality of the wireless channel used in the transmission of the test data in the fourth wireless communication unit 203.

According to the present embodiment, a program is configured for causing a computer to execute the step S1101 of sequentially changing, by the first wireless communication unit 106, a wireless channel to transmit test data used for detecting communication quality of each of a plurality of wireless channels to the reception device 200; the step S1092 of transmitting, by the first wireless communication unit 106, still-image data generated from image data output from the imaging unit 101 to the reception device 200 when an image-recording instruction is received from a user; the step S107 of transmitting, by the second wireless communication unit 108, moving-image data generated from the image data to the reception device using a wireless channel different from the wireless channel currently used by the first wireless communication unit 106; and the step S117 of setting a wireless channel determined from communication quality information about the communication quality of the wireless channel used in the transmission of the test data in the second wireless communication unit 108.

According to the present embodiment, a program is configured for causing a computer to execute the step S2111 of sequentially changing, by the third wireless communication unit 201, a wireless channel to receive test data used for detecting communication quality of each of a plurality of wireless channels from the endoscope 100; the step S2121 of receiving, by the third wireless communication unit 201, still-image data from the endoscope 100; the step S210 of receiving, by the fourth wireless communication unit 203, moving-image data from the endoscope 100 using a wireless channel different from the wireless channel used by the third wireless communication unit 201; and the step S2188 of setting a wireless channel determined from communication quality information about the communication quality of the wireless channel used in the transmission of the test data in the fourth wireless communication unit 203.

In the present embodiment, it is possible to perform moving-image transmission more stably because moving-image data and still-image data are transmitted on different wireless channels. It is possible to perform moving-image transmission more stably by setting a wireless channel determined from communication quality information about communication quality of a wireless channel used in the transmission of test data in the second wireless communication unit 108 or the fourth wireless communication unit 203.

In the first operation example and the second operation example, it is possible to perform the transmission of still-image data and the acquisition of information about communication quality of a wireless channel used in the transmission of still-image data in parallel by sequentially changing the wireless channel to transmit the still-image data.

In the third operation example and the fourth operation example, it is possible to transmit still-image data using a wireless channel having best communication quality by transmitting the still-image data using a fixed wireless channel.

In the first to fourth operation example, it is possible to perform moving-image transmission more stably using the wireless channel determined from the communication quality information in the transmission of moving-image data when the communication quality of the wireless channel used in the transmission of the moving-image data is less than predetermined quality.

In the first to fourth operation examples, the reception device 200 can perform the process according to a type of data by transmitting information for identifying the test data and the still-image data to the reception device 200.

Although embodiments of the present invention have been described above with reference to the drawings, specific configurations are not limited to the embodiments, and a design change, etc. may also be included without departing from the scope of the present invention. The present invention is not to be considered as being limited by the foregoing description, and is only limited by the scope of the appended claims.

What is claimed is:
1. An endoscope, comprising:
an image sensor configured to image a subject and output image data;
a moving-image converter configured to generate moving-image data from the image data output from the image sensor;
a still-image converter configured to generate still-image data from the image data output from the image sensor;
a release instruction receiver configured to receive an image-recording instruction from a user;
a first wireless communicator configured to sequentially change a wireless channel to transmit test data used for detecting communication quality of each of a plurality of wireless channels to a reception device and transmit the still-image data to the reception device when the release instruction receiver receives the image-recording instruction;
a second wireless communicator configured to transmit the moving-image data to the reception device using a wireless channel different from the wireless channel currently used by the first wireless communicator; and
a first processor configured to set a wireless channel in the second wireless communicator, wherein the wireless channel is determined from communication quality information regarding the communication quality of the wireless channel used in the transmission of the test data,
wherein the communication quality information regarding the communication quality of the wireless channel used in the transmission of the test data is indicated by a communication data rate of the wireless channel used in the transmission of the test data.

2. The endoscope according to claim 1, wherein the first wireless communicator sequentially changes the wireless channel at a previously designated time interval to transmit the still-image data to the reception device, when the release instruction receiver receives the image-recording instruction.

3. The endoscope according to claim 1, wherein the first wireless communicator transmits the still-image data to the reception device using only one wireless channel, when the release instruction receiver receives the image-recording instruction.

4. The endoscope according to claim 1,
wherein the first wireless communicator or the second wireless communicator receives wireless channel information indicating a wireless channel determined from the communication quality information from the reception device, and wherein the first processor sets the wireless channel indicated by the wireless channel information in the second wireless communicator.

5. The endoscope according to claim 1, wherein the first wireless communicator or the second wireless communicator receives reception information indicating that the test data is received from the reception device, and
wherein the first processor generates the communication quality information on the basis of the reception information, determines a wireless channel on the basis of the generated communication quality information, and sets the determined wireless channel in the second wireless communicator.

6. The endoscope according to claim 1, wherein the first processor sets the wireless channel determined from the communication quality information in the second wireless communicator, when the communication quality of the wireless channel used by the second wireless communicator is less than predetermined quality.

7. The endoscope according to claim 1, wherein the first wireless communicator transmits information used for identifying the test data and the still-image data to the reception device.

8. A wireless endoscope system including an endoscope and a reception device,
wherein the endoscope incudes:
an image sensor configured to image a subject and output image data;
a moving-image converter configured to generate moving-image data from the image data output from the image sensor;
a still-image converter configured to generate still-image data from the image data output from the image sensor;
a release instruction receiver configured to receive an image-recording instruction from a user;
a first wireless communicator configured to sequentially change a wireless channel to transmit test data used for detecting communication quality of each of a plurality of wireless channels to a reception device and transmit the still-image data to the reception device when the release instruction receiver receives the image-recording instruction;
a second wireless communicator configured to transmit the moving-image data to the reception device using a wireless channel different from the wireless channel currently used by the first wireless communicator; and
a first processor configured to set a wireless channel in the second wireless communicator, the wireless channel being determined from communication quality information regarding the communication quality of the wireless channel used in the transmission of the test data, and
wherein the reception device includes:
a third wireless communicator configured to sequentially change a wireless channel to receive the test data and receive the still-image data;
a fourth wireless communicator configured to receive the moving-image data using a wireless channel different from the wireless channel used by the third wireless communication unit; and
a second processor configured to set a wireless channel determined from the communication quality information in the fourth wireless communication unit,
wherein the communication quality information regarding the communication quality of the wireless channel used in the transmission of the test data is indicated by a communication data rate of the wireless channel.

* * * * *